(12) United States Patent
Gillberg et al.

(10) Patent No.: US 9,320,446 B2
(45) Date of Patent: Apr. 26, 2016

(54) BIOELECTRIC SENSOR DEVICE AND METHODS

(71) Applicant: Medtronic, Inc., Minneapolis, MN (US)

(72) Inventors: Jeffrey Gillberg, Coon Rapids, MN (US); Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 175 days.

(21) Appl. No.: 14/227,719

(22) Filed: Mar. 27, 2014

(65) Prior Publication Data

US 2015/0157225 A1    Jun. 11, 2015

Related U.S. Application Data

(60) Provisional application No. 61/913,759, filed on Dec. 9, 2013.

(51) Int. Cl.
*A61B 5/0408* (2006.01)
*A61B 5/04* (2006.01)
*A61B 5/00* (2006.01)

(52) U.S. Cl.
CPC ............... *A61B 5/04* (2013.01); *A61B 5/04085* (2013.01); *A61B 5/04087* (2013.01); *A61B 5/683* (2013.01); *A61B 5/6805* (2013.01); *A61B 5/6823* (2013.01); *A61B 5/6832* (2013.01); *A61B 2562/046* (2013.01); *A61B 2562/164* (2013.01)

(58) Field of Classification Search
CPC ...................... A61B 5/04085; A61B 2562/046
USPC .......................... 600/372, 382, 386, 391–393
See application file for complete search history.

(56) References Cited

U.S. PATENT DOCUMENTS

| 4,233,987 A | 11/1980 | Feingold |
| 4,428,378 A | 1/1984 | Anderson et al. |
| 4,497,326 A | 2/1985 | Curry |

(Continued)

FOREIGN PATENT DOCUMENTS

| EP | 1 072 284 A2 | 1/2001 |
| EP | 1 504 713 A1 | 2/2005 |

(Continued)

OTHER PUBLICATIONS

International Search Report / Written Opinion, issued Aug. 6, 2014; Patent Application No. PCT/US2014/036153, filed Apr. 30, 2014; 14 pages.
International Search Report / Written Opinion, issued Nov. 7, 2014; Patent Application No. PCT/US2014/036163, filed Apr. 30, 2014; 12 pages.
International Search Report / Written Opinion, issued Oct. 28, 2014; Patent Application No. PCT/US2014/041928, filed Jun. 11, 2014; 15 pages.
International Search Report / Written Opinion, issued Oct. 24, 2014; Patent Application No. PCT/US2014/041929, filed Jun. 11, 2014; 15 pages.
U.S. Appl. No. 14/173,288, filed Feb. 5, 2014, Sambelashvili.

(Continued)

*Primary Examiner* — Lee S Cohen
(74) *Attorney, Agent, or Firm* — Carol F. Barry

(57) ABSTRACT

Various embodiments of a bioelectric sensor device for sensing bioelectric data from a human body are disclosed. The device can include a flexible substrate, a plurality of sensors arranged in a sensor array on a sensor array portion of the substrate, an electrically conductive network located on the substrate, and a plurality of lines of weakness formed in the sensor array portion of the substrate. In one or more embodiments, each line of weakness is configured to enhance separation of the sensor array portion of the substrate along a separation line that extends between at least two sensors of the plurality of sensors. The device can also include a left reference electrode proximate a distal end of a left reference electrode arm of the substrate and a right reference electrode proximate a distal end of a right reference electrode arm of the substrate.

28 Claims, 12 Drawing Sheets

(56) References Cited

U.S. PATENT DOCUMENTS

| | | |
|---|---|---|
| 4,566,456 A | 1/1986 | Koning et al. |
| 4,674,511 A | 6/1987 | Cartmell |
| 4,763,660 A * | 8/1988 | Kroll .................. A61B 5/04085 439/77 |
| 5,052,388 A | 10/1991 | Sivula et al. |
| 5,054,496 A | 10/1991 | Wen et al. |
| 5,311,873 A | 5/1994 | Savard et al. |
| 5,443,492 A | 8/1995 | Stokes et al. |
| 5,514,163 A | 5/1996 | Markowitz et al. |
| 5,628,778 A | 5/1997 | Kruse et al. |
| 5,671,752 A | 9/1997 | Sinderby et al. |
| 5,683,432 A | 11/1997 | Goedeke et al. |
| 5,810,740 A | 9/1998 | Paisner |
| 5,891,045 A | 4/1999 | Albrecht et al. |
| 5,922,014 A | 7/1999 | Warman et al. |
| 6,055,448 A | 4/2000 | Anderson et al. |
| 6,187,032 B1 | 2/2001 | Ohyu et al. |
| 6,236,883 B1 | 5/2001 | Ciaccio et al. |
| 6,311,089 B1 | 10/2001 | Mann et al. |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,473,638 B2 | 10/2002 | Ferek-Petric |
| 6,480,745 B2 | 11/2002 | Nelson et al. |
| 6,507,756 B1 | 1/2003 | Heynen et al. |
| 6,532,379 B2 * | 3/2003 | Stratbucker ........ A61B 5/04085 600/382 |
| 6,584,343 B1 | 6/2003 | Ransbury et al. |
| 6,599,250 B2 | 7/2003 | Webb et al. |
| 6,640,136 B1 | 10/2003 | Helland et al. |
| 6,772,004 B2 | 8/2004 | Rudy |
| 6,804,555 B2 | 10/2004 | Warkentin |
| 6,847,836 B1 * | 1/2005 | Sujdak .................. A61B 5/6841 600/382 |
| 6,856,830 B2 | 2/2005 | He |
| 6,882,882 B2 | 4/2005 | Struble et al. |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 8,010,194 B2 | 8/2011 | Muller |
| 8,019,402 B1 * | 9/2011 | Kryzpow ........... A61B 5/04085 600/386 |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,617,082 B2 | 12/2013 | Zhang et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,805,504 B2 | 8/2014 | Sweeney |
| 2002/0161307 A1 | 10/2002 | Yu et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0122479 A1 | 6/2004 | Spinelli et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0253162 A1 | 11/2006 | Zhang et al. |
| 2007/0142871 A1 | 6/2007 | Libbus et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099619 A1 | 4/2009 | Lessmeier et al. |

(56) References Cited

U.S. PATENT DOCUMENTS

| | | |
|---|---|---|
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054560 A1 | 3/2011 | Rosenberg et al. |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0304407 A1 | 11/2013 | George et al. |
| 2013/0324828 A1* | 12/2013 | Nishiwaki .......... A61B 5/04085 600/391 |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032172 A1 | 1/2015 | Ghosh |
| 2015/0032173 A1 | 1/2015 | Ghosh |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0265840 A1 | 9/2015 | Ghosh et al. |

FOREIGN PATENT DOCUMENTS

| | | |
|---|---|---|
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 98/26712 A1 | 6/1998 |
| WO | WO 00/45700 | 8/2000 |
| WO | WO 01/67950 A1 | 9/2001 |
| WO | WO 2005/056108 A2 | 6/2005 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/013994 A3 | 4/2007 |
| WO | WO 2007/139456 A1 | 12/2007 |
| WO | WO 2008/151077 A2 | 12/2008 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | PCT/US2014/036153 | 4/2014 |
| WO | PCT/US2014/036163 | 4/2014 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

Hayes et al., "Cardiac Resynchronization Therapy and the Relationship of Percent Biventricular Pacing to Symptoms and Survival," *Heart Rhythm*, Sep. 2011; 8(9):1469-1475.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Vardas et al., The Task Force for Cardiac Pacing and Cardiac Resynchronization Therapy of the European Society of Cardiology.

(56) References Cited

OTHER PUBLICATIONS

Developed in Collaboration with the European Heart Rhythm Association, *European Heart Journal*, 2007; 28:2256-2295.
International Search Report and Written Opinion issued May 3, 2012 for International Application No. PCT/US2012/036262; 9 pages.
International Search Report and Written Opinion issued May 3, 2012 for International Application No. PCT/US2012/036302; 9 pages.
International Search Report and Written Opinion issued on Apr. 8, 2015, for International Application No. PCT/US2014/069070; 11 pages.
U.S. Appl. No. 13/916,353, filed Jun. 12, 2013, Ghosh.
U.S. Appl. No. 13/916,377, filed Jun. 12, 2013, Ghosh.
U.S. Appl. No. 13/952,043, filed Jul. 26, 2013, Ghosh.
U.S. Appl. No. 13/952,061, filed Jul. 26, 2013, Ghosh.
U.S. Appl. No. 14/190,508, filed Feb. 26, 2014.
U.S. Appl. No. 14/190,578, filed Feb. 26, 2014.
U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/227,919, filed Mar. 27, 2014, Ghosh et al.
U.S. Appl. No. 14/227,955, filed Mar. 27, 2014, Ghosh et al.
U.S. Appl. No. 14/227,962, filed Mar. 27, 2014, Ghosh et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.
International Search Report and Written Opinion for PCT/US2014/036262, dated May 3, 2012; 9 pg.
International Search Report and Written Opinion for PCT/US2014/036302, dated May 3, 2012; 9 pg.
"CardioGuide System Enables Real-Time Navigation of Left Ventricular Leads During Medtronic CRT Implants," Press Release, Apr. 9, 2013, Medtronic, Inc., 2 pgs.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
"Heart Failure Management" datasheet [online]. Medtronic, Minneapolis, Minnesota, [Last updated on Jun. 3, 2013].Retrieved from the Internet: www.medtronic.com; 9 pages.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Sweeney et al., "Analysis of Ventricular Activation Using Surface Electrocardiography to Predict Left Ventricular Reverse Volumetric Remoldeling During Cardiac Resynchronization Therapy," *Circulation*, Feb. 9, 2010; 121(5):626-34. Available online Jan. 25, 2010.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Varma et al., "Placebo CRT," *Journal of Cardiovascular Electrophysiology*, vol. 19, Aug. 2008; p. 878.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
International Search Report and Written Opinion issued on Jun. 11, 2015 for International Application No. PCT/US2015/021442; 13 pages.
International Search Report and Written Opinion for PCT/US2014/0247583, issued Nov. 4, 2014; 7 pages.
International Search Report and Written Opinion issued on Nov. 12, 2014 for International Application No. PCT/US2014/047971; 7 pages.
International Search Report and Written Opinion issued on Nov. 12, 2014 for International Application No. PCT/US2014/048120; 7 pages.
Cuculich et al., "The Electrophysiological Cardiac Ventricular Substrate in Patients After Myocardial Infarction," *J. Am. Coll. Cardiol.*, 2011; 58:1893-1902.
Dawoud et al., "Inverse Electrocardiographic Imaging to Assess Electrical Dyssynchrony in Cardiac Resynchronization Therapy Patients," *Computing in Cardiology*, 2012; 39:993-996.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Medtronic Vitatron CARELINK ENCORE® Programmer Model 29901 Reference Manual, 2013, Medtronic, Inc., Minneapolis, MN.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Strik et al., "Electrical and Mechanical Ventricular Activation During Left Bundle Branch Block and Resynchronization," *J. of Cardiovasc. Trans. Res.*, 2012; 5:11-126.
International Search Report and Written Opinion issued on Mar. 9, 2015, for International Application No. PCT/US2014/069214.
International Search Report and Written Opinion issued on Mar. 17, 2015, for International Application No. PCT/US2014/069192.
International Search Report and Written Opinion issued on Mar. 16, 2015, for International Application No. PCT/US2014/069182.

* cited by examiner

BIOELECTRIC SENSOR DEVICE AND METHODS

CROSS-REFERENCE TO RELATED APPLICATIONS

This application claims the benefit of U.S. Provisional Patent Application No. 61/913,759, filed Dec. 9, 2013, and entitled "BIOELECTRIC SENSOR DEVICE AND METHODS," which is incorporated herein by reference in its entirety.

The present disclosure provides various embodiments of bioelectric sensor devices and systems that utilize such devices for sensing bioelectric data from a human body.

BACKGROUND

Various systems and devices can be used for sensing bioelectric data from a human body. For example, multi-electrode electrocardiogram (ECG) systems can be utilized for body-surface potential mapping by recording simultaneous ECG measurements from multiple sensors or electrodes applied to selected locations of a patient's body. These sensors may be included in apparatus such as vests, bands, belts, straps, patches, wearable garments, t-shirts, bras, hats (e.g., for neural signals), etc.

Some ECG systems include multiple sensors generally arranged as part of a vest that is attached to a patient. These vests can be applied to a patient's torso for receiving bioelectric signals and, in some configurations, delivering stimulating signals to the patient. Bioelectric signals from the patient are detected by the sensors and transmitted via conductive paths to a medical monitoring system or apparatus such as an ECG base unit.

For example, one type of electrode vest is described in U.S. Pat. No. 6,055,448 to Anderson et al., entitled SENSOR DEVICE. The described device includes a plurality of finger-like substrate portions of a flexible dielectric material that are releasably attachable to the thoracic region of a human body.

Further, for example, U.S. Patent Publication No. 2013/0018251 to Caprio et al., entitled SENSOR DEVICE WITH FLEXIBLE JOINTS, describes a sensor device that includes a flexible dielectric substrate, a plurality of sensors distributed on the substrate, and an electrically conductive network distributed on the substrate connecting the sensors to a terminal portion of the substrate. Integrated flexible joints permit a certain amount of elasticity in and allow relative movement between at least two of the sensors when the sensor device is placed onto the human body.

Such vests are generally provided in multiple sizes to accommodate various body types and sizes of patients. For example, U.S. Patent Publication No. 2011/0190615 to Phillips et al., entitled ELECTRODE PATCH MONITORING DEVICE, describes an electrode patch monitoring device that includes an array of electrodes formed on a flexible substrate. The electrode patch monitoring device may be available in a plurality of sizes.

SUMMARY

The present disclosure provides various embodiments of bioelectric sensor devices and systems that utilize such devices for sensing bioelectric data from a human body.

In one aspect, the present disclosure provides a bioelectric sensor device for sensing bioelectric data from a human body. The bioelectric sensor device includes a flexible dielectric substrate including a first major surface and a second major surface, where the substrate further includes a sensor array portion including a center, a left reference electrode arm including a proximal end and a distal end, a right reference electrode arm including a proximal end and a distal end, and a contact array arm including a proximal end and a distal end. The proximal end of the contact array arm is attached to the sensor array portion of the substrate. The device further includes a plurality of sensors arranged in a sensor array on the sensor array portion of the substrate, where each sensor of the plurality of sensors is configured to sense bioelectric data when in contact with skin; and an electrically conductive network located on the substrate, where the electrically conductive network includes a plurality of electrically conductive paths, where each electrically conductive path of the plurality of electrically conductive paths extends from one sensor of the plurality of sensors to a contact array on the contact array arm, and where the contact array includes a plurality of contacts on the contact array arm proximate the distal end of the contact array arm. The device further includes a left reference electrode proximate the distal end of the left reference electrode arm and a right reference electrode proximate the distal end of the right reference electrode arm, where the left reference electrode is electrically connected to a contact in the contact array and the right reference electrode is electrically connected to a contact in the contact array; and a plurality of lines of weakness formed in the sensor array portion of the substrate, where each line of weakness of the plurality of lines of weakness is configured to enhance separation of the sensor array portion of the substrate along a separation line that extends between at least two sensors of the plurality of sensors.

In one or more embodiments, the sensor array portion of the substrate includes a left edge, a right edge, a top edge extending from the left edge to the right edge, and a bottom edge extending from the left edge to the right edge, where a first line of weakness of the plurality of lines of weakness extends between the top edge and the bottom edge of the sensor array portion, and further where a first sensor of the plurality of sensors is located between the first line of weakness and the left edge of the sensor array portion such that separation of the substrate along the first line of weakness removes the first sensor from the device.

In one or more embodiments, a second line of weakness of the plurality of lines of weakness extends between the top edge and the bottom edge of the sensor array portion, where a second sensor of the plurality of sensors is located between the second line of weakness and the first line of weakness such that separation of the substrate along the second line of weakness removes the second sensor from the device.

In one or more embodiments, a third line of weakness of the plurality of lines of weakness extends between the top edge and the bottom edge of the sensor array portion, where a third sensor of the plurality of sensors is located between the third line of weakness and the second line of weakness such that separation of the substrate along the third line of weakness removes the third sensor from the device.

In one or more embodiments, a fourth line of weakness of the plurality of lines of weakness extends between the first line of weakness and the second line of weakness such that separation of the substrate along the first, second, and fourth lines of weakness removes the second sensor of the plurality of sensors from the device without removing the first sensor and where an electrically conductive path of the plurality of electrically conductive paths that extends from the first sensor to the contact array remains after separation of the second sensor.

In one or more embodiments, a fifth line of weakness of the plurality of lines of weakness extends between the left edge and the center of the sensor array portion, where any of the lines of weakness of the plurality of lines of weakness that extend between the top edge and the bottom edge of the sensor array portion between the left edge and the center of the sensor array portion intersect the fifth line of weakness.

In one or more embodiments, at least one sensor of the plurality of sensors is located between the fifth line of weakness and the top edge of the sensor array portion and where at least one sensor of the plurality of sensors is located between the fifth line of weakness and the bottom edge of the sensor array portion.

In one or more embodiments, a sixth line of weakness of the plurality of lines of weakness extends between the right edge and the center of the sensor array portion, where any of the lines of weakness of the plurality of lines of weakness that extend between the top edge and the bottom edge of the sensor array portion between the right edge and the center of the sensor array portion intersect with the sixth line of weakness.

In one or more embodiments, at least one sensor of the plurality of sensors is located between the sixth line of weakness and the top edge of the sensor array portion and where at least one sensor of the plurality of sensors is located between the sixth line of weakness and the bottom edge of the sensor array portion.

In one or more embodiments, the device can include at least one alignment marker positioned on the substrate and extending between the top edge and the bottom edge of the sensor array portion at the center of the sensor array portion.

In one or more embodiments, the at least one alignment marker includes radiopaque material.

In one or more embodiments, the sensor array portion of the substrate includes a left edge, a right edge, a top edge extending from the left edge to the right edge, and a bottom edge extending from the left edge to the right edge, where the proximal end of the left reference electrode arm and the proximal end of the right reference electrode arm are attached to the sensor array portion of the flexible dielectric substrate.

In one or more embodiments, the proximal end of the left reference electrode arm and the proximal end of the right reference electrode arm are attached to the bottom edge of the sensor array portion of the flexible dielectric substrate.

In one or more embodiments, the proximal end of the left reference electrode arm and the proximal end of the right reference electrode arm are attached to the top edge of the sensor array portion of the flexible dielectric substrate.

In one or more embodiments, the proximal end of the left reference electrode arm is located inside the plurality of lines of weakness such that the left reference electrode arm remains attached to the sensor array portion of the flexible dielectric substrate after separation of the sensor array portion along any line of weakness of the plurality of lines of weakness.

In one or more embodiments, the proximal end of the right reference electrode arm is located inside the plurality of lines of weakness such that the right reference electrode arm remains attached to the sensor array portion of the flexible dielectric substrate after separation of the sensor array portion along any line of weakness of the plurality of lines of weakness.

In one or more embodiments, the proximal end of the left reference electrode arm and the proximal end of the right reference electrode arm are attached to the contact array arm of the flexible dielectric substrate.

In one or more embodiments, the sensor array portion of the substrate includes a left edge, a right edge, a top edge extending from the left edge to the right edge, and a bottom edge extending from the left edge to the right edge, where the proximal end of the contact array arm is attached to the bottom edge of the sensor array portion.

In one or more embodiments, the contact array arm includes adhesive on the second major surface of the substrate proximate the proximal end of the contact array arm.

In one or more embodiments, the flexible dielectric substrate can include a second left reference electrode arm including a proximal end and a distal end, and a second right reference electrode arm including a proximal end and a distal end.

In one or more embodiments, the device can include a second left reference electrode proximate the distal end of the second left reference electrode arm and a second right reference electrode proximate the distal end of the second right reference electrode arm, where the second left reference electrode is electrically connected to a contact in the contact array and the second right reference electrode is electrically connected to a contact in the contact array.

In one or more embodiments, the sensor array portion of the substrate includes a left edge, a right edge, a top edge extending from the left edge to the right edge, and a bottom edge extending from the left edge to the right edge, where the proximal end of the second left reference electrode arm and the proximal end of the second right reference electrode arm are attached to the sensor array portion of the flexible dielectric substrate.

In one or more embodiments, the proximal end of the second left reference electrode arm and the proximal end of the second right reference electrode arm are attached to the bottom edge of the sensor array portion of the flexible dielectric substrate.

In one or more embodiments, the proximal end of the second left reference electrode arm and the proximal end of the second right reference electrode arm are attached to the top edge of the sensor array portion of the flexible dielectric substrate.

In one or more embodiments, the proximal end of the second left reference electrode arm is located inside the plurality of lines of weakness such that the second left reference electrode arm remains attached to the sensor array portion of the flexible dielectric substrate after separation of the sensor array portion along any line of weakness of the plurality of lines of weakness.

In one or more embodiments, the proximal end of the second right reference electrode arm is located inside the plurality of lines of weakness such that the second right reference electrode arm remains attached to the sensor array portion of the flexible dielectric substrate after separation of the sensor array portion along any line of weakness of the plurality of lines of weakness.

In one or more embodiments, the bioelectric sensor device can be used in a method of removing a sensor of the plurality of sensors from a bioelectric sensor device. The method includes providing the bioelectric sensor device, where the sensor array portion of the substrate includes a left edge, a right edge, a top edge extending from the left edge to the right edge, and a bottom edge extending from the left edge to the right edge. The method further includes separating the sensor array portion of the substrate along a line of weakness of the plurality of lines of weakness extends between the top edge and the bottom edge of the sensor array portion, where the sensor is located between the line of weakness and the left edge of the sensor array portion.

In one or more embodiments, the method can include removing an additional sensor of the plurality of sensors by separating the sensor array portion of the substrate along an additional line of weakness that extends between the top edge and the bottom edge of the sensor array portion, where the additional sensor is located between the additional line of weakness and the right edge of the sensor array portion.

These and other aspects of the present disclosure will be apparent from the detailed description below. In no event, however, should the above summaries be construed as limitations on the claimed subject matter, which subject matter is defined solely by the attached claims, as may be amended during prosecution.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

BRIEF DESCRIPTION OF THE DRAWINGS

Throughout the specification, reference is made to the appended drawings, where like reference numerals designate like elements, and wherein.

DETAILED DESCRIPTION

Figure 1A:
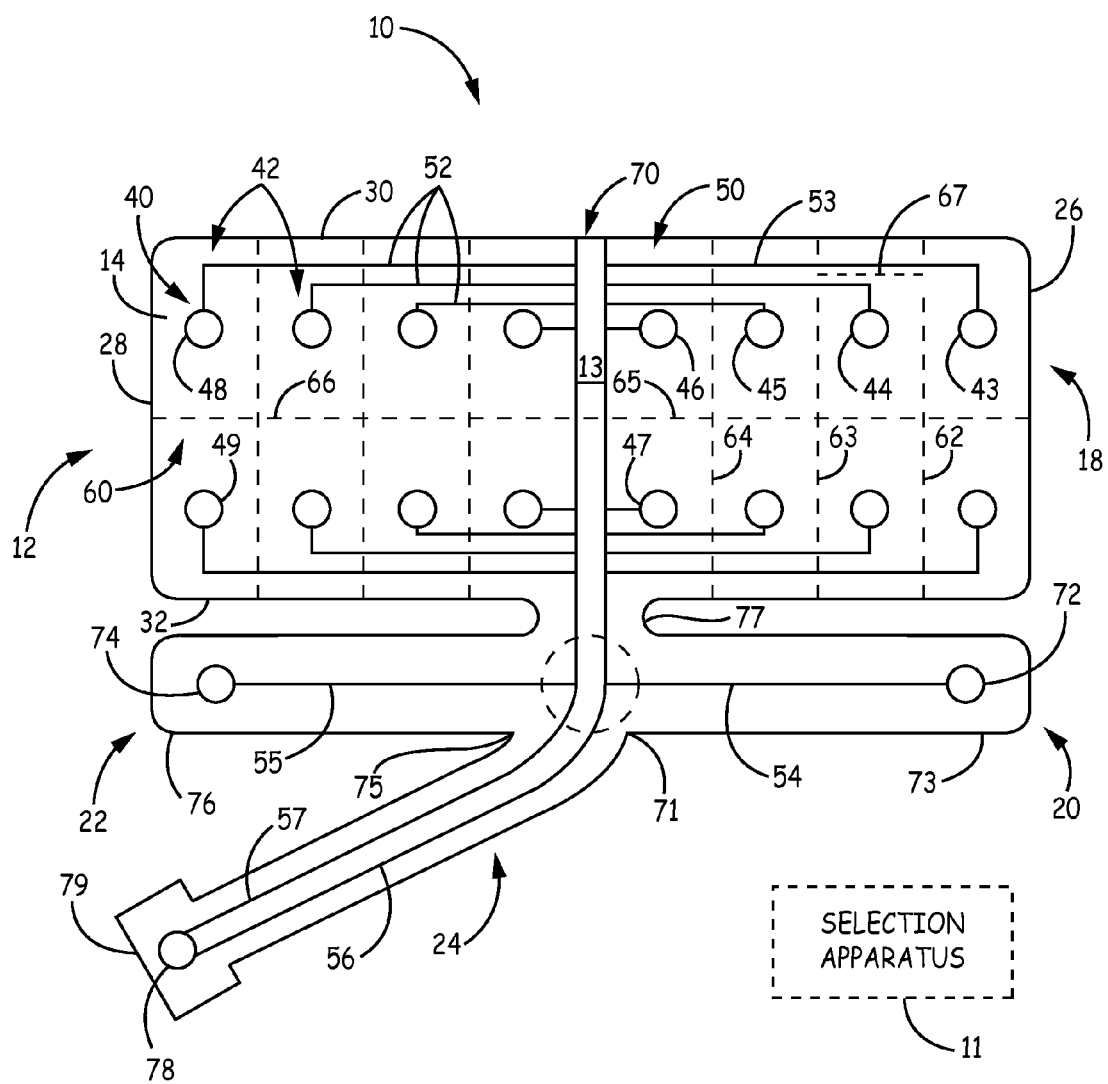
FIGS. 1A-B are schematic plan views of one embodiment of a bioelectric sensor device.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present disclosure.

In general, the present disclosure provides various embodiments of bioelectric sensor devices and systems that include such devices. In one or more embodiments, the devices can be used for sensing bioelectric data from a human body. Further, in one or more embodiments, the devices can be used to help determine whether a patient will benefit from cardiac resynchronization therapy (CRT). If a patient is a viable candidate for such therapy, then one or more embodiments of the disclosed devices can be used to aid in placement of one or more leads of an implantable medical device and monitor cardiac activity to fine tune pacing and sensing parameters of the implanted device.

In one or more embodiments, a bioelectric sensor device for sensing bioelectric data from a human body includes as described herein one or more lines of weakness formed in a sensor array portion of a substrate of the device. Each line of weakness can be configured to enhance separation of the sensor array portion of the substrate along a separation line that extends between at least two sensors located on the substrate such that the device can be appropriately sized to match a particular patient's body. When appropriately sized, the sensors of the device may, in one or more embodiments, be more accurately placed upon the patient's body.

Figure 1B:
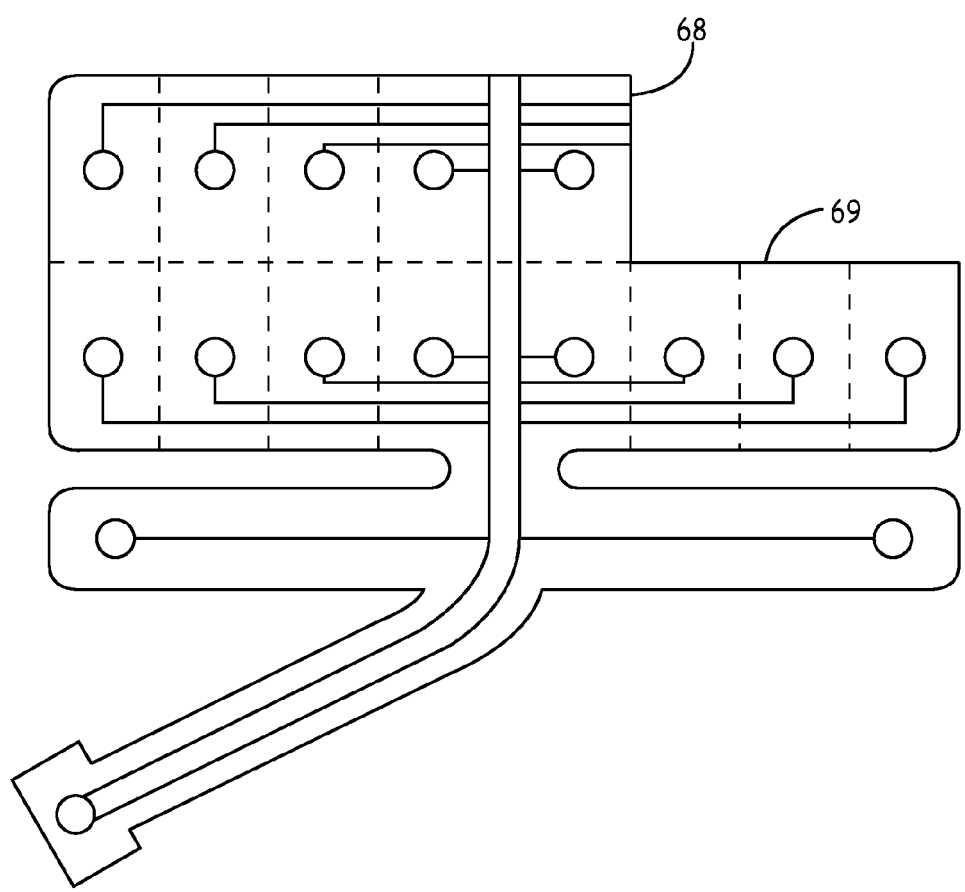

For example, FIGS. 1A-B are schematic plan views of one embodiment of a bioelectric sensor device 10 for sensing bioelectric data from a human body. The sensor device 10 includes a substrate 12 that includes a first major surface 14 and a second major surface (not shown). The substrate 12 can be constructed of any suitable material or materials, e.g., polymeric, rubber, natural fiber, etc. In one or more embodiments, the substrate 12 can include polyester (e.g., MYLAR), polyethylene foam, polyester non-woven materials, cellulose rayon non-woven materials, and polyethylene vinyl acetate films. In one or more embodiments, the substrate 12 can include a flexible dielectric substrate. The substrate 12 can be transparent, translucent, and/or opaque in one or more areas.

In the illustrative embodiment of FIGS. 1A-B, the substrate 12 includes a sensor array portion 18, a left reference electrode arm 20, a right reference electrode arm 22, and a contact array arm 24 attached to the sensor array portion 18 of the substrate. As used herein, the terms "left" and "right" refer to features viewed from the perspective of a patient upon which the device 10 is applied. For example, in one or more embodiments, the left reference electrode arm 20 is configured to be positioned on a left anterior surface or left posterior surface of a torso of a patient or the left arm/leg of the patient.

In one or more embodiments, the sensor array portion 18 includes a left edge 26, a right edge 28, a top edge 30 extending from the left edge to the right edge, a bottom edge 32 extending from the left edge to the right edge, and a center 13. As used herein, the term "top edge" refers to an edge of the sensor array portion 18 of the substrate 12 that is adjacent an upper surface (either anterior or posterior) of a torso of a patient when the sensor device 10 is positioned on the patient. Further, as used herein, the term "bottom edge" refers to an edge of the sensor array portion 18 of the substrate 12 that is adjacent a lower surface (anterior or posterior) of a patient when the sensor device 10 is positioned on the patient.

The sensor array portion 18 can take any suitable shape or shapes, e.g., polygonal, ovoid, circular. In the illustrative embodiment, the sensor array portion 18 of the substrate 12 is generally rectangular with round edges. In one or more alternative embodiments, the corners can be any suitable shape, e.g., right angle, etc.

The sensor array portion 18 can have any suitable dimensions. In one or more embodiments, the sensor array portion 18 can be sized such that a sensor array 40 located on the sensor array portion of the substrate 12 can be positioned in the desired location on a patient's body, e.g., a torso as is further described herein.

The left reference electrode arm 20 includes a proximal end 71 and a distal end 73, and the right reference electrode arm 22 also includes a proximal end 75 and a distal end 76. The left and right reference electrode arms 20, 22 of the substrate 12 can also take any suitable shape or shapes and have any suitable dimensions. In the illustrative embodiment, the left and right reference electrode arms 20, 22 are generally rectangular with round edges. In one or more embodiments, the left and right reference electrode arms 20, 22 can be formed from the same material as the sensor array portion 18 such that they are continuous with the sensor array portion of the substrate 12. In one or more alternative embodiments, the left and right reference electrode arms 20, 22 can be attached to the sensor array portion 18 of the substrate 12 and can be constructed of the same material as that of the sensor array portion or different material.

The left and right reference electrode arms 20, 22 can be positioned in any suitable location and orientation relative to the sensor array portion 18. For example, in one or more embodiments, the proximal ends 71, 75 of the left and right arms 20, 22 can be attached to the contact array arm 24 such that the arms are adjacent to and spaced apart from the sensor array portion 18 along the contact array arm 24 as is illustrated in FIGS. 1A-B. In one or more alternative embodiments, the proximal ends 71, 75 of the left and right arms 20, 22 can be attached to the sensor array portion 18 as is further described herein.

The substrate 12 also includes the contact array arm 24. The contact array arm 24 includes a proximal end 77 attached to the bottom edge 32 of the sensor array portion 18 and a distal end 79. The contact array arm 24 can include any suitable material or materials, e.g., the same materials as the substrate 12. In one or more embodiments, the contact array arm 24 and the sensor array portion 18 are formed from the same continuous piece of material. In one or more alternative embodiments, the contact array arm 24 is made from a separate piece of material and attached to the sensor array portion 18. In such embodiments, the contact array arm 24 can include the same material as the sensor array portion 18 or different material from the sensor array portion.

The contact array arm 24 can take any suitable shape or shapes. In the illustrated embodiment, the contact array arm 24 is curved and extends in a direction away from the center 13 of the sensor array portion 18. The contact array arm 24 of the substrate 12 can have any suitable dimensions. In one or more embodiments, the contact array arm 24 can be of sufficient length such that it can extend beyond a surgical gown or blanket draped over a patient and reach a medical monitoring system or apparatus to provide a connection to the system as is further described herein.

The sensor device 10 further includes a plurality of sensors (e.g., electrodes) 42 arranged in a sensor array 40 on or in the sensor array portion 18 of the substrate 12. In one or more embodiments, each sensor of the plurality of sensors 42 is configured to sense bioelectric data when in contact with skin of a patient.

The sensors 42 can be positioned or formed on the second major surface of the substrate 12 such that they are positioned between the substrate and skin of a patient. In one or more alternative embodiments, the sensors 42 can be positioned or formed on the first major surface 14 of the substrate 12, and one or more openings or vias can be formed in the substrate that coincide with the sensors such that the sensors can contact skin of a patient. In such embodiments, a protective layer can be positioned on the sensor array 40 such that the array is positioned between the protective layer and the substrate 12.

In one or more embodiments, one or more of these openings or vias can be formed by separating the substrate 12 along a line of weakness. For example, the sensor array portion 18 of the substrate 12 can be separated along a separation line 68 (as shown in FIG. 1B) while leaving a sensor of the plurality of sensors 42 in place between the separation line and the left edge 26 of the sensor array portion 18.

The plurality of sensors 42 of the sensor array 40 can include any suitable sensor that is configured to sense bioelectric data when in contact with skin of a patient. Any suitable number of sensors 42 can be included in the sensor array 40. In one or more embodiments, at least twelve sensors 42 are included in the array 40. In one or more alternative embodiments, at least fifty sensors 42 are included in the array 40. In one or more alternative embodiments, at least 256 sensors 42 are include in the array 40. And in one or more alternative embodiments, no greater than 256 sensors 42 are included in the array 40.

In one or more embodiments, the plurality of sensors 42 can be configured to surround the heart of a patient and record, or monitor, the electrical signals associated with the depolarization and repolarization of the heart after the signals have propagated through the torso of the patient. Each of the sensors 42 can be used in a unipolar configuration to sense the torso surface potentials that reflect the cardiac signals. In one or more embodiments, the sensor array 40 can be used to evaluate electrical dyssynchrony in the heart of the patient. In such embodiments, the sensors 42 of the sensor array 40 can be positioned over the torso of the patient, including, e.g., the anterior, lateral, and posterior surfaces of the torso of the patient. A medical monitoring system or apparatus (not shown) attached to a contact array 78 can record and analyze the torso surface potential signals sensed by the sensors.

The plurality of sensors 42 of the sensor array 40 can be formed using any suitable technique or combination of techniques. For example, in one or more embodiments, the plurality of sensors 42 can be formed on the substrate 12 using flexographic printing with conductive inks or chemical etching of metals.

The plurality of sensors 42 can be positioned in any suitable arrangement on the sensor array portion 18 of the substrate 12. For example, although the sensors of the plurality of sensors 42 are arranged in a linear array, including two rows of sensors arranged from left to right, in one or more alternative embodiments, the sensors can be arranged in any other suitable configuration, e.g., a single linear row of sensors, three or more linear rows of sensors, one or more rows of sensors with non-linear spacing to provide a higher density of sensors in one region of the torso (e.g. left side of the torso proximate the heart), one or more rows of sensors with positioning corresponding to standard precordial lead positions, and sensors configured in geometric grid patterns such as a triangular, hexagonal, etc.

Figure 12:
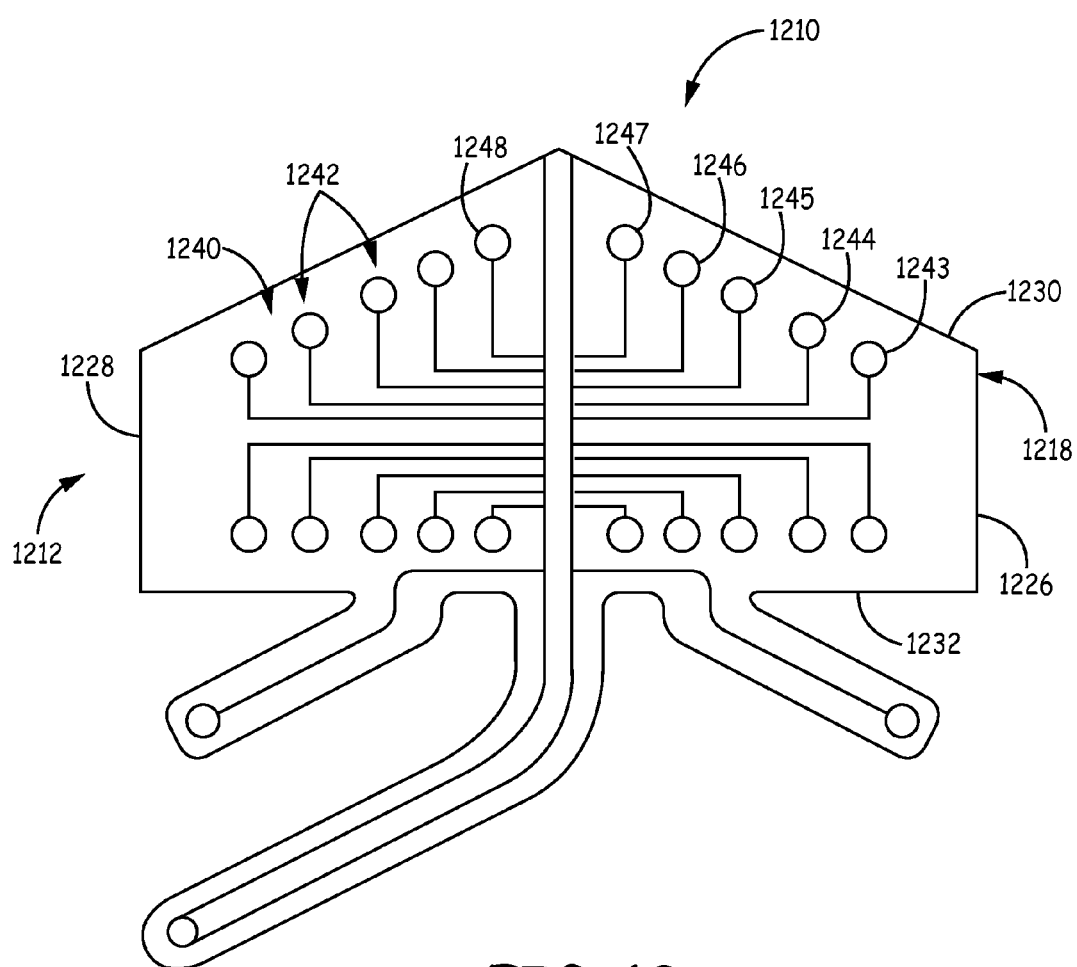
FIG. 12 is a schematic plan view of another embodiment of a bioelectric sensor device.

For example, FIG. 12 is a schematic plan view of one embodiment a bioelectric sensor device 1210. All of the design considerations and possibilities regarding device 10 of FIGS. 1A-C apply equally to device 1210 of FIG. 12.

Figure 1C:
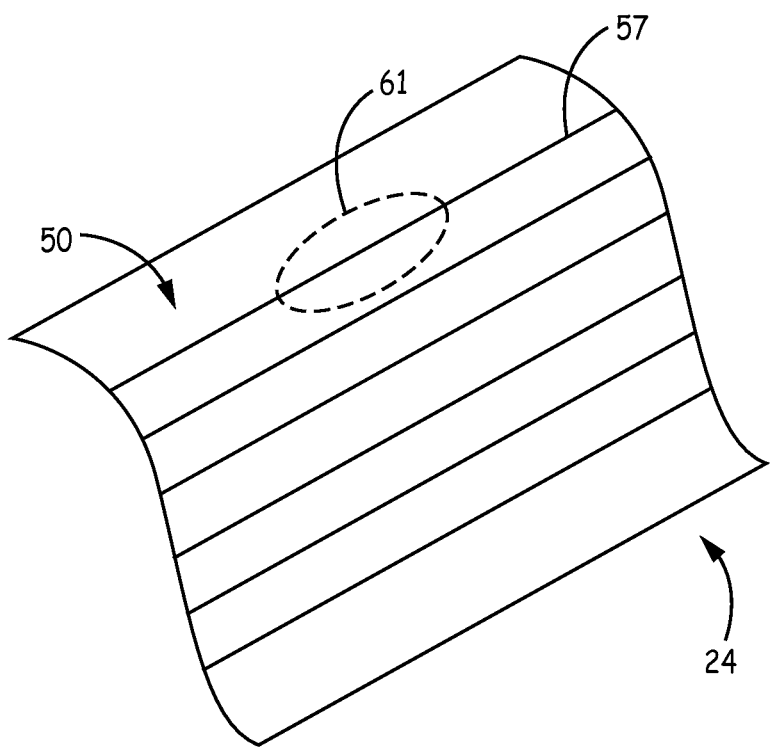
FIG. 1C is an enlarged schematic plan view of a portion of a contact array arm of the bioelectric sensor device of FIGS. 1A-B.

One difference between the device 1210 of FIG. 12 and the device 10 of FIGS. 1A-C is that a distance between a top edge 1230 and a bottom edge 1232 of a sensor array portion 1218 decreases in a direction from a center 1213 to a left edge 1226 of the sensor array portion. Further, in one or more embodiments, a distance between the top edge 1230 and the bottom edge 1232 decreases in a direction from the center 1213 to a right edge 1228 of the sensor array portion 1218. And in one or more embodiments, the distance between the top edge 1230 and the bottom edge 1232 can decrease in both directions from the center 1213 to the left and right edges 1226, 1228 of the sensor array portion 1218.

Another difference between devices 1210 and 10 is that several sensors 1242 are positioned to provide precordial leads. For example, sensors 1243-1248 are positioned such that they are aligned anatomically with the location of precordial leads. Further, in one or more embodiments, this tapering of the top edge 1230 of device 1210 may leave room for a left-sided or right-sided implant pocket as is known in the art.

Returning, to FIGS. 1A-C, an electrically conductive network 50 can be located on or in the substrate 12. The electrically conductive network 50 includes a plurality of electrically conductive paths 52, where each electrically conductive path of the plurality of electrically conductive paths extends from one sensor 42 of the plurality of sensors 40 to a contact array 78 located on the contact array arm 24 as is further described herein. The contact array 78 includes a plurality of contacts. In one or more embodiments, each sensor of the plurality of sensors 42 can be electrically connected to a contact in the contact array 78. In one or more embodiments, the conductive paths 52 can be continuous from the sensors 42 to the contact array 78. Alternatively, in one or more embodiments, one or more conductive paths can connect a sensor to a connecting pad (not shown) positioned on the sensor array portion 18 of the substrate 12 or at any suitable location along the contact array arm 24. Additional conductive paths can then electrically connect the connecting pad to the contact array 78 on the contact array arm 24. The plurality of electrically conductive paths 52 have been combined in FIGS. 1A-B for clarity and illustrative purposes only as the paths 52 are too small to be individually shown.

The electrically conductive paths 52 can include any suitable conductive material or materials, e.g., metal, carbon, graphite, or combinations thereof. In one or more embodiments, nanotubes or conductive flakes or particles (e.g., formed of metal, carbon, graphite, other suitable conductive materials, or combinations thereof) can act as a conductor and be provided within a matrix or carrier. In one or more embodiments, the electrically conductive paths 52 can include an insulating coating that may be provided on or over the conductive material, where the coating can be made from electrically conductive material that can be used as a shielding layer to minimize any interference from unwanted transient signals. And the paths 52 can take any suitable shape and include any suitable dimensions.

The conductive paths 52 of the electrically conductive network 50 can be formed using any suitable technique or combination of techniques. For example, in one or more embodiments, the conductive paths 52 can be formed on the substrate 12 using flexographic printing with conductive inks or chemical etching of metals.

The plurality of electrically conductive paths 52 of the electrically conductive network 50 can be formed in any suitable pattern. In the embodiment illustrate in FIGS. 1A-B, the electrically conductive paths are disposed on the substrate 12 in a pattern where the paths extend from a sensor of the plurality of sensors 42 to the center 13 of the sensor array portion 18 along a path proximate either the top edge 30 or the bottom edge 32 such that the conductive paths are between the sensors 42 and the top or bottom edges. As used herein, the term "proximate the top edge" means that an element or feature is located closer to the top edge than to the bottom edge of the sensor array portion. And the term "proximate the bottom edge" means that an element or feature is located closer to the bottom edge than the top edge of the sensor array portion.

Figure 3:
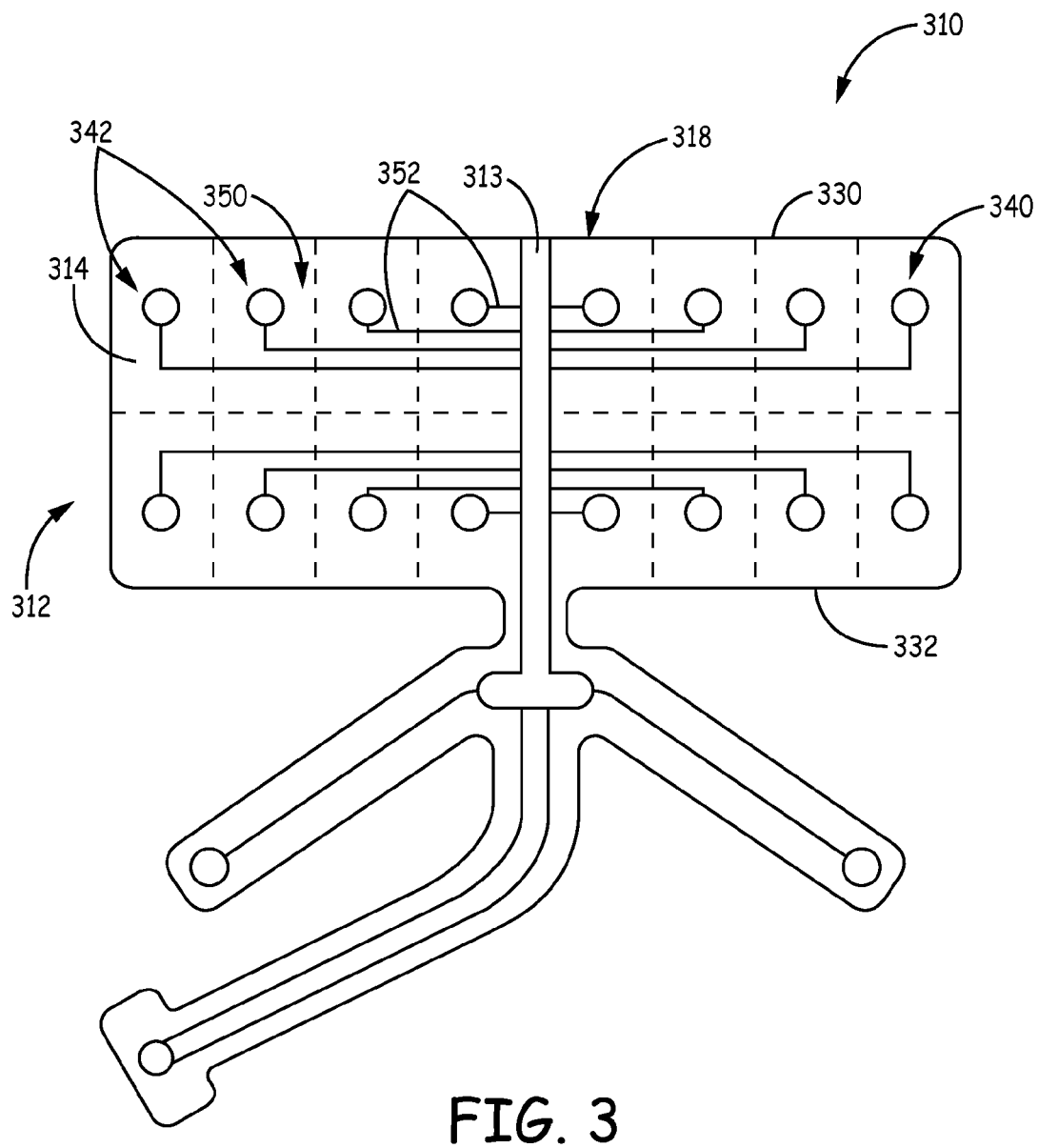
FIG. 3 is a schematic plan view of another embodiment of a bioelectric sensor device.

In an alternative embodiment illustrated in FIG. 3, conductive paths 352 of device 310 are disposed on substrate 312 such that they extend from a sensor of the plurality of sensors 342 of a sensor array 340 to a center 313 of a sensor array portion 318 along a path proximate the center of the sensor array portion such that the sensors 342 are between the conductive paths 352 and a nearest top or bottom edge 330, 332. As used herein, the term "proximate the center of the sensor array portion" means that an element or feature is closer to the center of the sensor array portion than to the top edge, bottom edge, left edge, or right edge of the sensor array portion. All of the design considerations and possibilities regarding the substrate 12, the plurality of sensors 42 of the sensor array 40, and the electrically conductive network 50 of the sensor device 10 of FIGS. 1A-C apply equally to the substrate 312, the plurality of sensors 342 of the sensor array 340, and the electrically conductive network 350 of the sensor device 310 of FIG. 3.

Returning to FIGS. 1A-B, the sensor device 10 also includes a plurality of lines of weakness 60 formed in the sensor array portion 18 of the substrate 12. Each line of weakness of the plurality of lines of weakness 60 is configured to enhance separation of the sensor array portion 18 of the substrate 12 along a separation line (e.g., separation lines 68, 69 of FIG. 1B) that extends between at least two sensors of the plurality of sensors 42. Any suitable number of lines of weakness can be formed in the sensor array portion 18 of the substrate 12.

The plurality of lines of weakness 60 can include any suitable structure or structures that enhance separation of the sensor array portion 18 of the substrate 12 along a separation line. For example, in one or more embodiments, the one or more lines of weakness of the plurality of lines of weakness 60 can be provided as a line of perforations. In one or more alternative embodiments, one or more lines of weakness of the plurality of lines of weakness 60 can include thinned portions of the substrate 12. And the plurality of lines of weakness 60 can be formed using any suitable technique or combination of techniques, e.g., kiss cutting, laser cutting, die cutting, rotary wheel cutting, punch cutting, water jet cutting/perforating, etc.

Although the lines of weakness are depicted as straight lines in the figures, these lines may also be curvilinear. In addition, in one or more embodiments, the lines of weakness can be formed in a rectangular grid. In one or more embodiments, the lines of weakness may form other geometrical patterns such as triangles, hexagons, or other patterns to allow for removal of one or more sensors.

In the illustrative embodiment of FIGS. 1A-B, the sensor device 10 includes a first line of weakness 62 of the plurality of lines of weakness 60 that extends between the top edge 30 and the bottom edge 32 of the sensor array portion 18. A first sensor 43 of the plurality of sensors 42 is located between the first line of weakness 62 and the left edge 26 of the sensor array portion 18 such that separation of the substrate 12 along the first line of weakness removes the first sensor from the device 10. The substrate 12 can be separated along the first line of weakness 62 or any line of weakness using any suitable technique or combination of techniques, e.g., pulling, tearing, ripping, cutting with a sharp instrument such as scissors or a knife, etc.

Further, the sensor device 10 includes a second line of weakness 63 of the plurality of lines of weakness 60 that extends between the top edge 30 and the bottom edge 32 of the sensor array portion 18. A second sensor 44 of the plurality of sensors 40 is located between the second line of weakness 63 and the first line of weakness 62 such that separation of the substrate 12 along the second line of weakness removes the second sensor from the device 10.

Still further, the device 10 includes a third line of weakness 64 of the plurality of lines of weakness 60 that extends between the top edge 30 and the bottom edge 32 of the sensor array portion 18. A third sensor 45 of the plurality of sensors 40 is located between the third line of weakness 64 and the second line of weakness 63 such that separation of the substrate 12 along the third line of weakness removes the third sensor from the device 10.

As shown in FIG. 1B, the substrate 12 has been separated along the third line of weakness 64 such that the first, second, and third sensors 43, 44, 45 have been removed from the sensor device 10. In one or more embodiments, the first, second, and third sensors 43, 44, 45 can be removed at the same time by separating the substrate 12 along the third line of weakness 64. Alternatively, the first and second sensors 43, 44 can be removed by separating the substrate along the second line of weakness 63, and the third sensor 45 can be removed by separating the substrate along the third line of weakness 64. In one or more alternative embodiments, the first sensor 43 can be removed by separating the substrate along the first line of weakness 62, the second sensor 44 can be removed by separating the substrate along the second line of weakness 63, and the third sensor 45 can be removed by separating the substrate along the third line of weakness 64.

One of skill in the art will understand that any suitable number of sensors of the plurality of sensors 42 can be removed by separating the substrate 12 along any suitable number of lines of weakness of the plurality of lines of weakness 60, e.g., a fourth sensor removed by separating the substrate along an additional line of weakness, etc.

In one or more embodiments, the device 10 can also include lines of weakness that extend between the left edge 26 of the substrate 12 and the center 13 of the sensor array portion 18. For example, the plurality of lines of weakness 60 includes a fifth line of weakness 65 that extends between the left edge 26 and the center 13 of the sensor array portion 18. In one or more embodiments, any of the lines of weakness of the plurality of lines of weakness 60 that extend between the top edge 30 and the bottom edge 32 of the sensor array portion 18 between the left edge 26 and the center 13 of the sensor array portion 18 can intersect with the fifth line of weakness 65, e.g., first, second, and third lines of weakness 62, 63, 64 can intersect the fifth line of weakness 65.

In one or more embodiments, at least one sensor 46 of the plurality of sensors 40 can be located between the fifth line of weakness 65 and the top edge 30 of the sensor array portion 18 of the substrate 12. In the illustrated embodiment, sensors 43, 44, and 45 are also located between the fifth line of weakness 65 and the top edge 30 of the sensor array portion 18 of the substrate 12. Any suitable number of sensors can be located between the fifth line of weakness 65 and the top edge 30. Further, in one or more embodiments, at least one sensor 47 of the plurality of sensors 42 can be located between the fifth line of weakness 65 and the bottom edge 32 of the sensor array portion 18 of the substrate 12. Any suitable number of sensors of the plurality of sensors 42 can be located between the fifth line of weakness 65 and the bottom edge 32.

In the illustrative embodiment of FIG. 1A, one or more of the sensors 43-46 can be removed from the sensor device 10 by separating the substrate 12 along the fifth line of weakness 65. Although not shown, an additional line of weakness of the plurality of lines of weakness 60 can be located in the center 13 of the sensor array portion 18 of the substrate 12 such that it extends between the top edge 30 and the bottom edge 32. Either a right portion (i.e., between the right edge 28 and the center 13) or a left portion (i.e., between the left edge 26 and the center 13) of the sensor array portion 18 can be removed along this central line of weakness.

In one or more embodiments, the plurality of lines of weakness 60 can include a sixth line of weakness 66 that extends between the right edge 28 and the center 13 of the sensor array portion 18. Any of the lines of weakness of the plurality of lines of weakness 60 that extend between the top edge 30 and the bottom edge 32 of the sensor array portion 18 between the right edge 28 and the center 13 of the sensor array portion 18 can intersect the sixth line of weakness 66. Further, in one or more embodiments, at least one sensor 48 of the plurality of sensors 42 is located between the sixth line of weakness 68 and the top edge 30 of the sensor array portion 18. In one or more embodiments, at least one sensor 49 of the plurality of sensors 40 can be located between the sixth line of weakness 68 and the bottom edge 32 of the sensor array portion 18.

In one or more embodiments, one or more additional lines of weakness of the plurality of lines of weakness 60 can be formed such that one or more sensors can be removed without disconnecting other sensors in the sensor array 40. For example, in one or more embodiments, to maintain electrically conductive path 53 to the first sensor 43, a fourth line of weakness 67 of the plurality of lines of weakness 60 may extend between the first line of weakness 62 and the second line of weakness 63 such that separation of the substrate 12 along this line of weakness and, e.g., the first, second, and fifth lines of weakness 62, 63, 65 removes the second sensor 44 from the sensor device 10 without removing the first sensor 43. The electrically conductive path 53, which extends from the first sensor 43 to the contact array 78, remains after separation of the second sensor 44. Additional lines of weakness between electrically conductive paths and/or between electrically conductive paths and one or more edges of the sensor array portion 18 can be included to maintain electrical connections while removing one or more selected sensors from the sensor array 40. In one or more embodiments, a sensor, e.g., second sensor 44, can be removed from the sensor array 42 to provide an opening in the sensor array portion 18 of the substrate 12 for surgical or diagnostic access to a torso of a patient.

The sensor device 10 can, in one or more embodiments, also include at least one alignment marker 70 that can be used to align the device to one or more anatomical features of a patient such that the sensor array 40 is positioned in a desired location. For example, the at least one alignment marker 70 can be configured to be aligned with the sternum of a patient when the sensor device 10 is positioned on an anterior surface of a torso of a patient such that, e.g., the sensor array portion 18 is symmetrical about the sternum. In one or more embodiments, the at least one alignment marker 70 can be configured to be aligned with the spine of a patient when the sensor device 10 is positioned on a posterior surface of a torso of a patient such that, e.g., the sensor array portion 18 is symmetrical about the spine.

The at least one alignment marker 70 can be positioned on or in the substrate 12 such that it extends between the top edge 30 and the bottom edge 32 of the sensor array portion 18 along the center 13 of the sensor array portion. The at least one alignment marker 70 can take any suitable shape and include any suitable dimensions. In one or more embodiments, the at least one alignment marker 70 can extend to one or both of the top edge 30 and bottom edge 32 of the sensor array portion 18.

The at least one alignment marker 70 can be formed using any suitable material or combination of materials, e.g., ink, foil, etc. In one or more embodiments, the at least one alignment marker 70 can be formed using radiopaque material and/or have echogenic or other properties so that it is visible using an appropriate imaging technique, e.g., fluoroscopy, computed tomography, magnetic resonance imaging, etc. The at least one alignment marker 70 can be made of platinum iridium, tungsten, barium sulfate, other radiopaque materials, and the like. In one or more embodiments, the at least one alignment marker 70 can also be constructed from materials impregnated with radiopaque or echogenic materials.

Although the embodiment depicted in FIGS. 1A-B includes a single alignment marker 70, any suitable number of alignment markers can be positioned on or in the substrate 12.

Figure 2A:
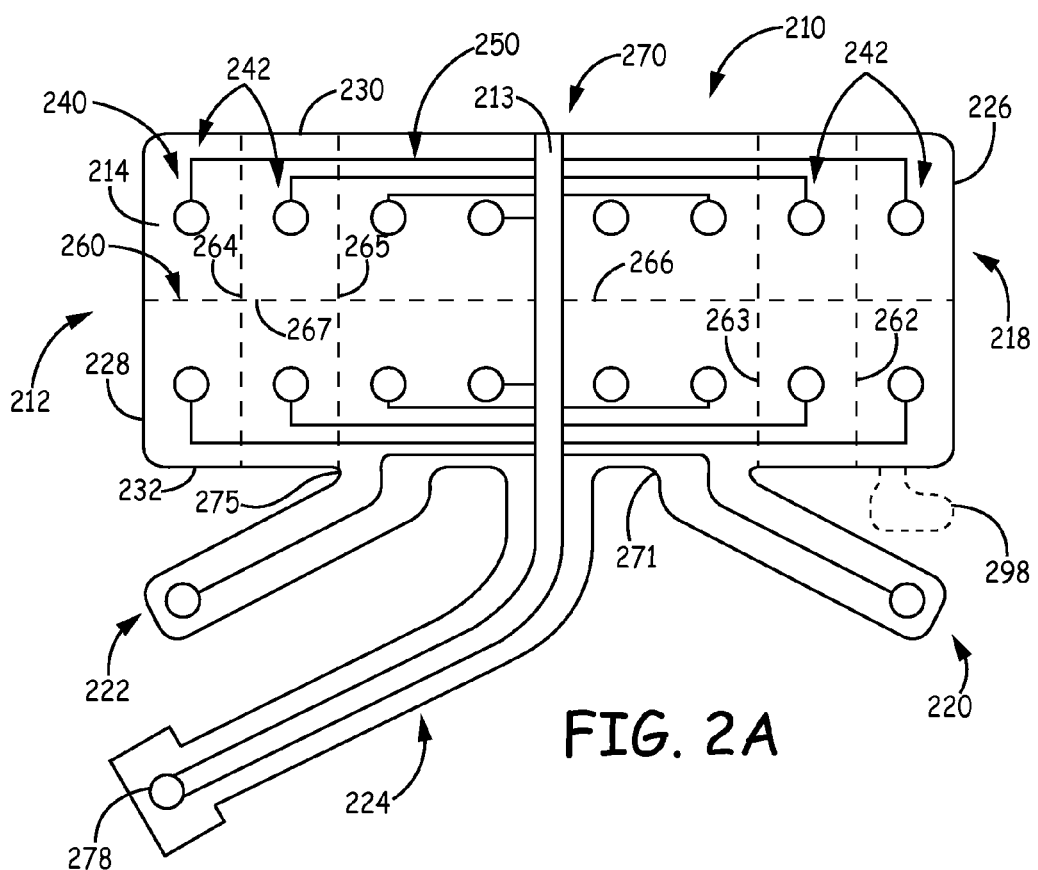
FIG. 2A is a schematic plan view of another embodiment of a first major surface of a bioelectric sensor device.
Figure 2B:
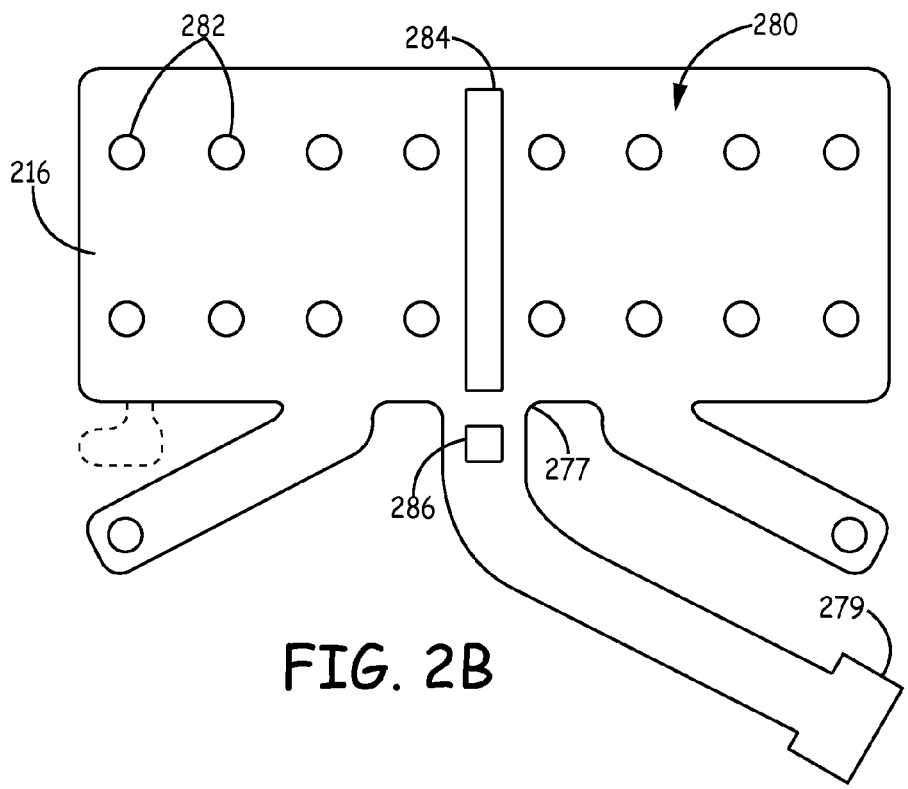
FIG. 2B is a schematic plan view of a second major surface of the bioelectric sensor device of FIG. 2A.
Figure 2C:
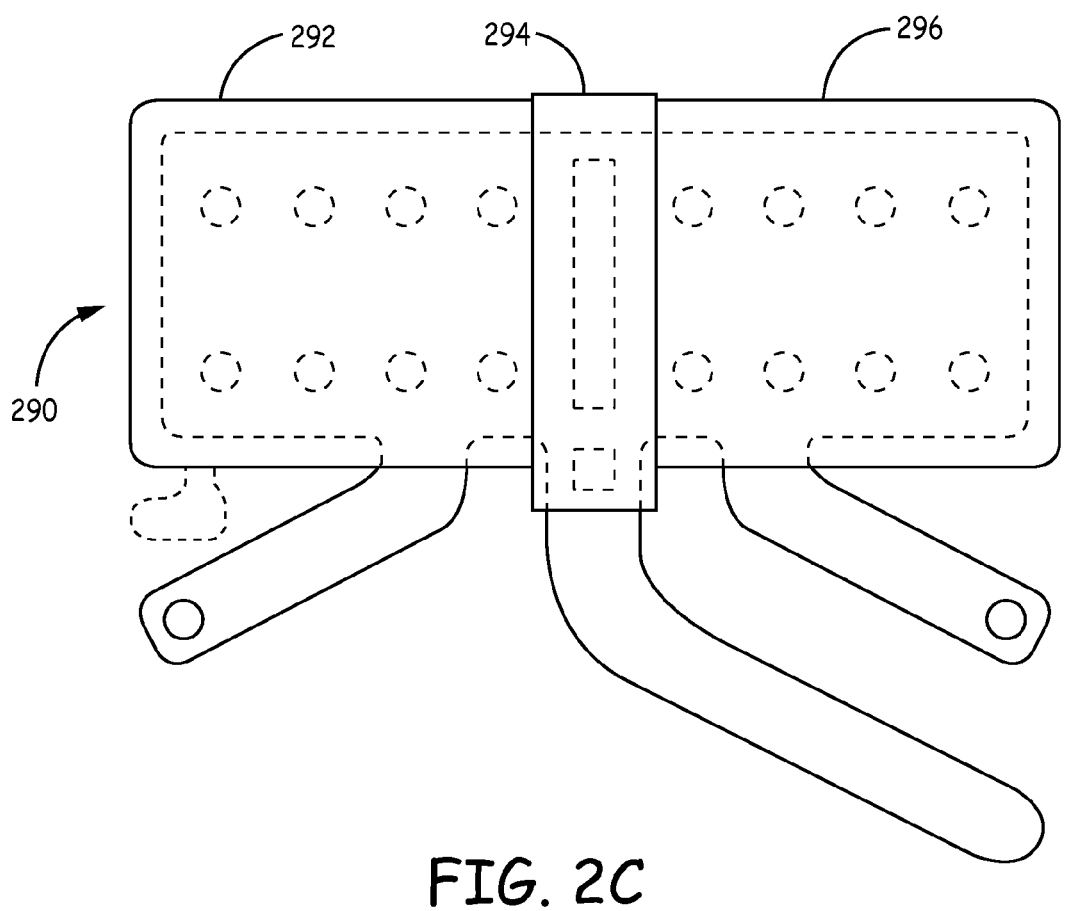
FIG. 2C is a schematic plan view of the second major surface of the bioelectric sensor device of FIG. 2A with a liner disposed over the second major surface.

Although not shown, the device 10 may, in one or more embodiments, include an adhesive layer disposed on the second major surface of the substrate 12 such that the device can be attached to skin of a patient after the device is positioned in the desired location relative to the patient (e.g., adhesive layer 280 of device 210 of FIGS. 2A-C). Further, the device 10 may, in one or more embodiments, include a liner positioned on the second major surface of the substrate 12 as is further described herein (e.g., liner 290 of device 210).

In one or more embodiments, datum marks or indicia can be provided on the sensor device 10 to assist in accurate and reproducible placement of the device on a patient. For example, each of the sensors of the plurality of sensors 42 can be numbered so that bioelectric data sensed by a particular sensor can be associated with the sensor. Further, for example, the left reference electrode arm 20 can include indicia that indicate that the arm is to be positioned, e.g., on the left leg of a patient, and the right reference electrode arm 22 can include indicia that indicate that the arm is to be positioned, e.g., on the right leg of the patient.

As mentioned herein, the substrate 12 of device 10 includes left and right reference electrode arms 20, 22. The proximal end 71 of the left reference electrode arm 20 is attached to the contact array arm 24 of the substrate 12. And the proximal end 75 of the right reference electrode arm 22 is attached to the contact array arm 24 of the substrate 12.

In one or more embodiments, a left reference electrode 72 is located on the left reference electrode arm 20 proximate the distal end 73, and a right reference electrode 74 is positioned on the right reference electrode arm 22 proximate the distal end 76. In this context, the term "proximate the distal end" means that an element or feature is located closer to the distal end of the left or right reference electrode arm than the proximal end of the left or right reference electrode arm. The left reference electrode arm 20 also includes a conductive path 54 that electrically connects the left reference electrode 72 to a contact in the contact array 78, and the right reference electrode arm 22 includes a conductive path 55 that connects the right reference electrode 74 to a contact in the contact array 78. Although depicted as including one electrode on each arm, 20, 22, two or more electrodes can be positioned on one or both of the left reference electrode arm 20 and the right reference electrode arm 22.

In general, the left and right reference electrodes 72, 74 can be positioned in any suitable location on a body of a patient. For example, in one or more embodiments, the left reference electrode 72 can be positioned on or adjacent to an anterior surface of a left leg of a patient. Further, in one or more embodiments, the right reference electrode 74 can be positioned on or adjacent to an anterior surface of a right leg of a patient.

In one or more embodiments, the sensor device 10 can include additional reference electrode arms. For example, the device 10 can include left and right reference electrode arms 20, 22, and left and right upper reference electrode arms (not shown) that are attached to the sensor array portion 18 at the top edge 30. In one or more alternative embodiments, left and right reference arms can be attached to the sensor array portion 18 at the left and right edges 26, 28 respectively. Each of the additional reference electrode arms can include one or more reference electrodes and conductive paths that connect the electrodes to contacts in the contact array 78 of the contact array arm 24.

As mentioned herein, the plurality of sensors 42 can be electrically connected to a contact in the contact array 78 located on or in the contact array arm 24 via the plurality of electrically conductive paths 52. The contact array 78 on the contact array arm 24 can include a plurality of contacts (not shown) arranged in any suitable array or position. The contacts of the contact array 78 have been combined in FIGS. 1A-B into a single contact as contact array 78 for clarity and illustrative purposes only as the individual contacts of the array would be too small for illustration. In one or more embodiments, the contact array 78 is disposed proximate the distal end 79 of the contact array arm 24. As used herein, the term "proximate the distal end of the contact array arm" means that the element or feature is located closer to the distal end 79 of the contact array arm 24 than to the proximal end 77 of the contact array arm.

In one or more embodiments, the contact array 78 may include a contact corresponding to each sensor of the plurality of sensors 42. The contact array 78 may, in one or more embodiments, include a contact for each reference electrode, e.g., reference electrodes 72, 74. In general, the contact array 78 is configured to electrically connect the sensor device 10 to a medical monitoring system or apparatus for collecting and/or analyzing the bioelectric data sensed by the sensor device 10.

As described herein, in one or more embodiments, one or more sensors of the plurality of sensors 42 of the sensor array 40 can be removed from the bioelectric sensor device 10 by separating the substrate along one or more lines of weakness of the plurality of lines of weakness 60. In one or more embodiments, one or more sensors of the plurality of sensors 42 can be turned off or disabled without physically removing the sensor from the device 10. For example, FIG. 1C is an enlarged schematic plan view of one portion of the contact array arm 24 of sensor device 10. This portion of the contact array arm 24 includes a line of weakness 61 that is configured to enhance separation of the contact array arm such that conductive path 57 is disrupted or disconnected. By separating the substrate 12 along line of weakness 61, a sensor that was electrically connected to a contact in the contact array 78 along conductive path 57 would no longer be electrically connected to the contact array, thereby in effect removing this sensor from the device 10.

The line of weakness 61 can take any suitable shape, e.g., ovoid, rectangular, triangular, etc. And in one or more embodiments, the line of weakness 61 can intersect one, two, or more conductive paths of the plurality of electrically conductive paths such that one, two or more sensors can be disconnected from the sensor array 78. Further, any suitable number of lines of weakness can be formed in the contact array arm 24 of the substrate 12 for disconnecting sensors from the sensor array 78.

In one or more embodiments, one or more sensors of the plurality of sensors 42 can be turned-off or disconnected from the sensor device 10 without physically removing the sensor from the sensor array 40 by optional selection apparatus 11. The selection apparatus 11 can include any suitable devices, circuits, or circuitry such that the apparatus is configured to selectively connect or disconnect one or more sensors of the plurality of sensors 40 to a suitable medical monitoring system or apparatus, e.g., physical switches, switch arrays, switch matrices, multiplexers, etc. The selection apparatus 11 can be positioned in any suitable location on the substrate 12, e.g., contact array arm 24. In one or more alternative embodiments, the selection apparatus 11 can be positioned separately from the substrate 12. Further, in one or more embodiments, the selection apparatus 11 can be a part of any suitable medical monitoring system or apparatus used with the sensor device 12.

In the illustrative embodiment of FIGS. 1A-B, the proximal ends 71, 75 of left and right reference electrode arms 20, 22 are attached to the contract array arm 24. The left and right reference electrode arms 20, 22 can, however, be positioned in any suitable location relative to the sensor array portion 18 of the substrate 12. For example, FIGS. 2A-C are schematic cross-section views of another embodiment of a bioelectric sensor device 210. All of the design considerations and possibilities regarding the device 10 of FIGS. 1A-C apply equally to the device 210 of FIGS. 2A-C. The sensor device 210 includes a flexible dielectric substrate 212 that includes a first major surface 214 and a second major surface 216. The substrate 212 also includes a sensor array portion 218, a left reference electrode arm 220, a right reference electrode arm 222, and a contact array arm 224 attached to the sensor array portion 218 of the substrate 212.

The device 210 also includes a plurality of sensors 242 arranged in a sensor array 240 on the sensor array portion 218, and an electrically conductive network 250 located on the substrate 212. The device 210 also includes a plurality of lines of weakness 260 formed in the sensor array portion 218 of the substrate 212, and at least one alignment marker 270.

One difference between the device 10 and the device 210 is that proximal ends 271, 275 of the left and right reference electrode arms 220, 222 are attached to the sensor array portion 218 of the substrate 212. Another difference between the device 10 and the device 210 is that the device 210 includes fewer lines of weakness of the plurality of lines of weakness 260 that extend from a top edge 230 to a bottom edge 232 of the sensor array portion 218 of the substrate 212.

For example, the plurality of lines of weakness 260 includes a first line of weakness 262, a second line of weakness 263, a third line of weakness 264, and a fourth line of weakness 265. Each of the lines of weakness 262-265 extends between the top edge 230 and the bottom edge 232 of the sensor array portion 218. Further, in one or more embodiments, the plurality of lines of weakness 260 includes a fifth line of weakness 266 that extends between a left edge 226 and a center 213 of the sensor array portion 218, and a sixth line of weakness 267 that extends between a right edge 228 and the center 213 of the sensor array portion 218.

The proximal end 271 of the left reference electrode arm 220 is attached to the sensor array portion 218 of the substrate 212 between the second line of weakness 263 and the center 213 of the sensor array portion 218, and the proximal end 275 of the right reference electrode arm 222 is attached to the sensor array portion between the fourth line of weakness 265 and the center 213 of the sensor array portion 218. In this illustrative embodiment, the first and second reference electrode arms 220, 222 are attached to the sensor array portion 218 in these locations so that these arms remain attached to the sensor array portion when the sensor array portion is separated along any of the lines of weakness 262-267. For example, the proximal end 271 of the left reference electrode arm 220 is located inside the plurality of lines of weakness 260 such that the left reference electrode arm remains attached to the sensor array portion 218 of the substrate 212 after separation of the sensor array portion along any line of weakness of the plurality of lines of weakness. And in one or more embodiments, the proximal end 275 of the right reference electrode arm 222 is located inside of the plurality lines of weakness 260 such that the right reference electrode arm remains attached to the sensor array portion 218 of the substrate 212 after separation of the sensor array portion along any line of weakness of the plurality of lines of weakness.

The device 210 also includes an adhesive layer 280 disposed on the second major surface 216 of the substrate 212 (FIG. 2B). The adhesive layer 280 can be a continuous layer of adhesive that is disposed on part of or over the entire second major surface 216 of the substrate 212. Alternatively, in one or more embodiments, the adhesive layer can be a patterned adhesive layer. For example, in the embodiment illustrated in FIG. 2B, the adhesive layer 280 is a patterned adhesive layer that includes discrete areas or islands of adhesive 282. In one or more embodiments, the discrete areas of adhesive 282 can be positioned such that they are aligned with one or more sensors of the plurality of sensors 242 in a direction transverse to the first and second major surfaces 214, 216 of the substrate 212. The patterned adhesive layer 280 can also include discrete area of adhesive 284 that is aligned with center 213 of the sensor array portion 218 of the substrate.

Further, in one or more embodiments, the adhesive layer 280 can include adhesive 286 on the second major surface 216 of the substrate proximate a proximal end 277 of the contact array arm 224. As used herein, the term "proximate the proximal end of the contact array arm" means that an element or feature (e.g., adhesive) is located closer to the proximal end 277 of the contact array arm 224 than to distal end 279 of the contact array arm. The adhesive 286 can attach the contact array arm 224 of the substrate 212 to skin of a patient to alleviate stress on the contract array arm.

The adhesive layer 280 can include any suitable adhesive. In one or embodiments, the adhesive layer can include a conductive adhesive such that the sensors of the plurality of sensors 242 are in electrical contact with the patient through the conductive adhesive. Any suitable conductive adhesive can be used for the adhesive layer, e.g., conductive hydrogels (e.g., polyethylene glycol, etc.), carbon impregnated pressure sensitive adhesive, etc. For example, in one or more embodiments, conductive hydrogels may include cationic acrylates, including, e.g., acrylic esters of quaternary chlorides and/or sulfates or acrylic amides of quaternary chlorides.

In one or more embodiments, the adhesive layer 280 can include conductive gel disposed on the second major surface 216 and aligned with one or more sensors of the plurality of sensors 242 to provide electrical contact between the sensors and skin of a patient, and a conductive or non-conductive adhesive disposed on the second major surface to attach the device 210 to skin of the patient. The conductive or non-conductive adhesive can be disposed in any suitable pattern on the second major surface 216, e.g., surrounding areas of conductive gel.

As mentioned herein, the devices of the present disclosure can include a liner that can protect the device prior to use. The liner can be removed before the device is attached to skin of a patient. For example, the embodiment illustrated in FIG. 2C includes a liner 290 disposed on the adhesive layer 280 such that the adhesive layer is between the liner and the second major surface 216 of the substrate 212. Any suitable liner can be used, e.g., polymer (e.g., polyethylene, polypropylene), plastic, rubber, natural fiber, polyester, etc. In one or more embodiments, the liner 290 may include a paper backing with a coating on one or both sides of the paper, where the coating may include silicone release agents that can provide a differential release.

The liner 290 can take any suitable shape and have any suitable dimensions. In one or more embodiments, the liner 290 can take the same shape as the sensor array portion to 18 of the substrate to 12. Further, in one or more embodiments, the liner 290 can include the same area as the sensor array portion to 18, or it can have a greater area or a lesser area than the area of the sensor array portion.

The liner 290 can be a continuous liner that covers most or all of the second major surface 216 of the substrate 212. Alternatively, in one or more embodiments, the liner 290 can be segmented such that a portion of the adhesive layer 280 can be exposed and applied to skin of a patient prior to removing additional portions of the liner. In the illustrative embodiment of FIG. 2C, the liner 290 includes a first portion 292 that is disposed over or on a portion of the sensor array portion 218 between the left edge 226 and the center 213, a second portion 294 that is disposed over or on the center 213 of the sensor array portion, and a third portion 296 disposed over or on a portion of the sensor array portion between the right edge 228 and the center 213. The central portion 294 of the liner 290 can also, in one or more embodiments, be disposed on the discrete area of adhesive 286 that is disposed on the contact array arm 224. In one or more alternative embodiments (not shown), the liner 290 may span a single row of sensors in any direction as one piece or in multiple pieces. The liner 290 may also be marked to distinguish it from the substrate (e.g. different colors and/or contrasting markings).

The embodiment of device 210 shown in FIGS. 2A-C can be applied to a patient by removing the central portion 294 of the liner 290 and attaching the center 213 of the sensor array portion 218 to the patient. The left and/or right portions 292, 296 of the liner 290 can then be removed such that the sensor array portion 218 can be attached to the patient. Alternatively, in one or more embodiments, the left or right portions 292, 296 of the liner 290 can be removed and the corresponding portion of the sensor array portion 218 can be attached to the patient, and the central portion 294 of the liner can then be removed to attached the center 213 of the sensor array portion 218 to the patient.

In one or more embodiments, a continuous liner 290 can be disposed on the adhesive layer 280, and the plurality of lines of weakness 260 can extend through the adhesive layer and also through the liner such that the liner includes one or more of the plurality of lines of weakness. In one or more alternative embodiments, one or more lines of weakness can be formed in the liner 290 prior to the liner being disposed on the adhesive layer 280.

The substrates of the sensor devices of the present disclosure can include additional portions that provide additional functionality. For example, one or more portions of the substrate can include additional arms that provide additional sensors or electrodes. In one exemplary embodiment shown in FIGS. 2A-C, a defibrillator electrode arm 298 (shown in broken lines) can be attached to the sensor array portion 218 of the substrate 212. The defibrillator electrode arm 298 can take any suitable shape and include any suitable dimensions, and can be attached to the sensor array portion 218 in any suitable location such that the defibrillator arm is positioned in the appropriate location. For example, the defibrillator arm 298 can be positioned over the heart of a patient such that appropriate treatment can be provided. The defibrillator electrode arm 298 can include one or more electrodes and conductive paths that electrically connect the one or more electrodes to one or more contacts of a contact array 278 on the contact array arm 224. An electrically conductive path for a defibrillator electrode may also be separate from the other sensor conductive paths for separate connection to a defibrillator instrument (not shown).

The sensor devices of the present disclosure can be positioned in any suitable location on a patient. In one or more embodiments, the sensor devices (e.g., device 10 of FIGS. 1A-C) can be positioned on an anterior surface of the torso of a patient. In one or more alternative embodiments, the sensor device can be positioned on a posterior surface of the torso of the patient.

Figure 4:
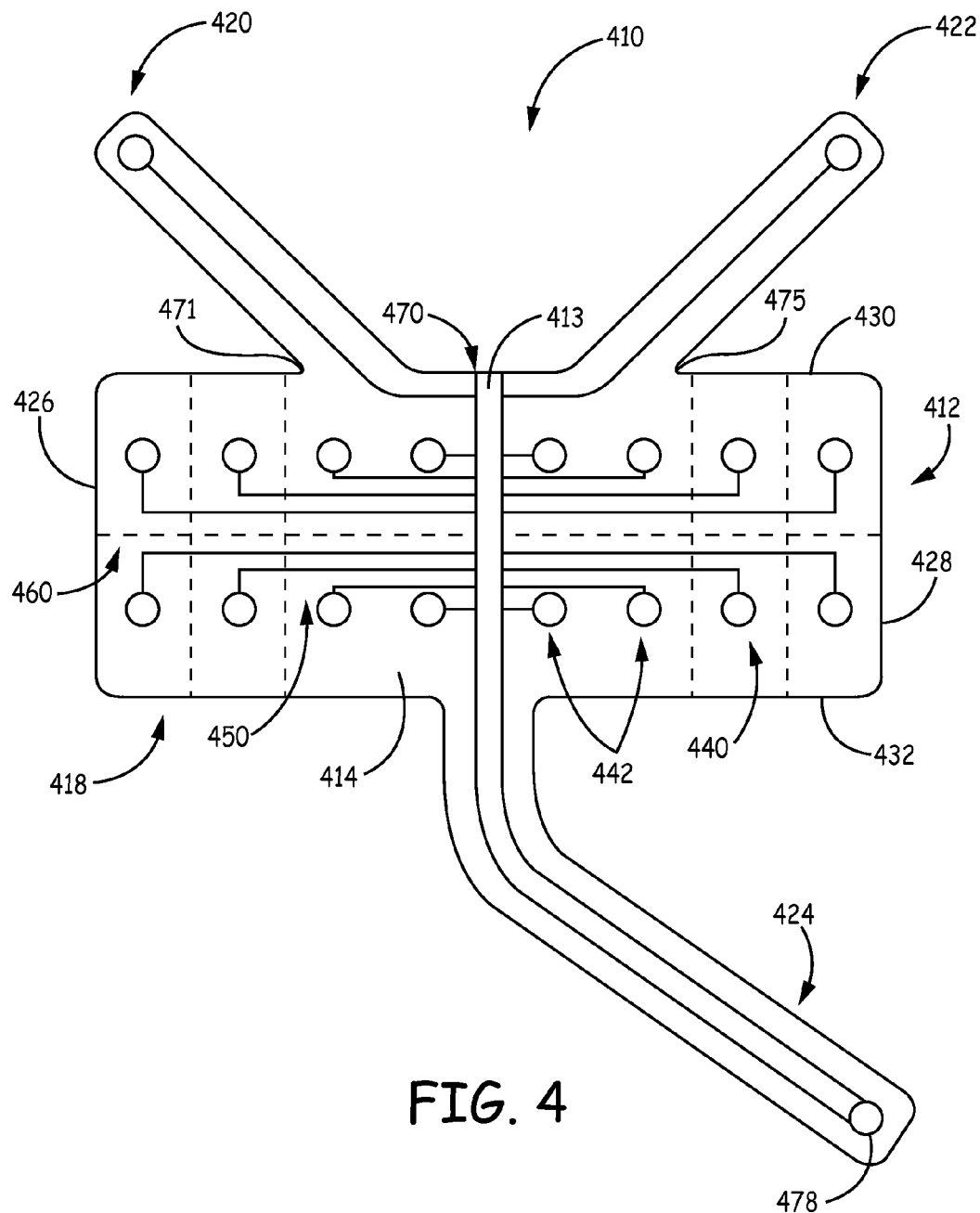
FIG. 4 is a schematic plan view of another embodiment of a posterior bioelectric sensor device.

For example, FIG. 4 is a schematic cross-section view of one embodiment of a posterior bioelectric sensor device 410. The device 410 is configured to be positioned on a posterior surface of a patient. All of the design considerations and possibilities regarding the device 10 of FIGS. 1A-C apply equally to the device 410 of FIG. 4. The device 410 includes a substrate 412 that includes a first major surface 414 and a second major surface (not shown). The substrate 412 also includes a sensor array portion 418, a left reference electrode arm 420, a right reference electrode arm 422, and a contact array arm 424 attached to the sensor array portion 418 of the substrate 412.

The device 410 also includes a plurality of sensors 442 arranged in a sensor array 440 on the sensor array portion 418 of the substrate 412, an electrically conductive network 450 also located on the sensor array portion, and a plurality of lines of weakness 460 formed in the sensor array portion of the substrate. The device 410 also includes at least one alignment marker 470 positioned on the substrate at a center 413 of the sensor array portion 418. Any suitable alignment marker can be used for the at least one alignment marker 470, e.g., at least one alignment marker 70 of device 10. In one or more embodiments, the at least one alignment marker 470 is configured to be aligned with a spine of a patient.

One difference between the sensor device 10 of FIGS. 1A-C and sensor device 410 of FIG. 4 is that proximal ends 471, 475 of the left and right reference electrode arms 420, 422 are attached to a top edge 430 of the sensor array portion 418. In other alternative embodiments, the proximal ends 471, 475 of the left and right reference electrode arms 420, 422 can be attached to a bottom edge 432 of the sensor array portion 418 of the substrate 412.

Another difference between device 10 and device 410 is that the contact array arm 424 of device 410 extends in a direction away from the center 413 of the sensor array portion 418 towards a right edge 428 of the sensor array portion 418. This is to allow a contact array 478 to connect to a computer and/or measurement apparatus on the same side of the patient as the contact array of an anterior bioelectric sensor device connects to the same computer and/or measurement apparatus (e.g., device 10 of FIGS. 1A-C).

The anterior and posterior bioelectric sensor devices described herein can be included in a system for sensing bioelectric data from a human body. For example, the bioelectric sensor device 10 of FIGS. 1A-C can be attached to an anterior surface of a torso of a patient, and the posterior bioelectric sensor device 410 of FIG. 4 can be attached to a posterior surface of the torso of the patient.

The anterior and posterior bioelectric sensor devices can be placed on a patient using any suitable technique or combination of techniques. In one or more embodiments, the posterior device can first be placed on a posterior surface of a torso of a patient, and then the anterior device can be place on an anterior surface of the torso. In one or more alternative embodiments, the anterior device can first be placed on an anterior surface of a torso of a patient, and then the posterior device can be placed on a posterior surface of the torso.

Figure 6:
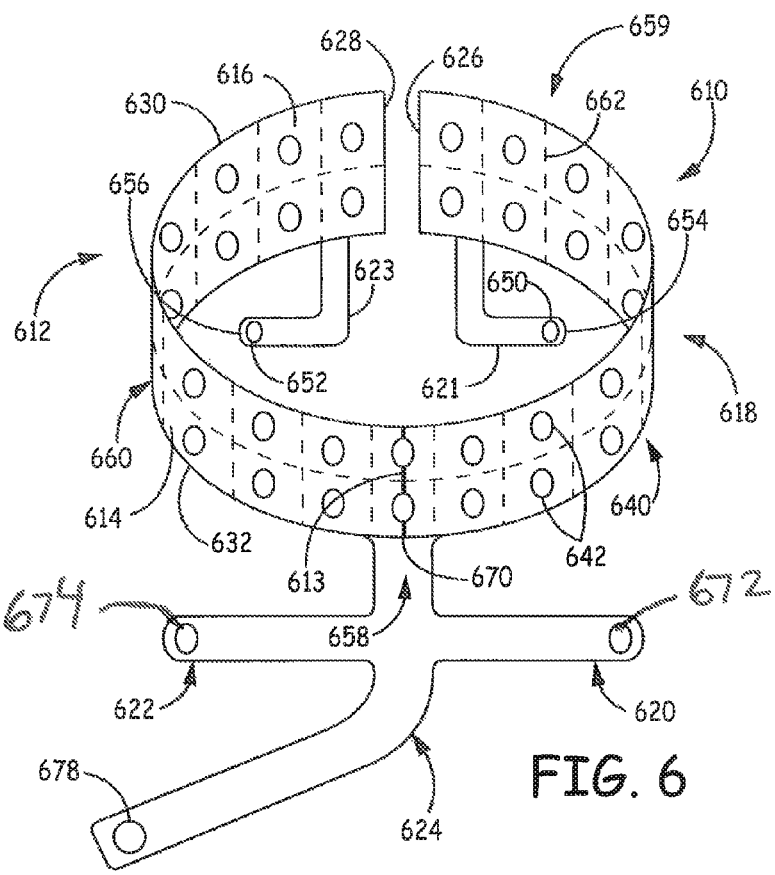
FIG. 6 is a schematic perspective view of another embodiment of a bioelectric sensor device.

In one or more embodiments, the bioelectric sensor device can include anterior and posterior portions that are connected or are continuous such that a unitary device can be attached to both an anterior and posterior surface of a torso of a patient. For example, FIG. 6 is a schematic perspective view of one embodiment of a bioelectric sensor device 610. All of the design considerations and possibilities regarding the device 10 of FIGS. 1A-C apply equally to the device 610 of FIG. 6. The sensor device 610 includes a flexible dielectric substrate 612 that includes a first major surface 614 and a second major surface 616. The substrate 612 also includes a sensor array portion 618, a left reference electrode arm 620, a right reference electrode arm 622, and a contact array arm 624 attached to the sensor array portion 618 of the substrate 612. The device 610 also includes a plurality of sensors 642 arranged in a sensor array 640 on the sensor array portion 618. The device 610 also includes a plurality of lines of weakness 660 formed in the sensor array portion 618 of the substrate 612. Further, the device 610 can include a left reference electrode 672 and a right reference electrode 674.

One difference between the device 10 and the device 610 is that the device 610 includes a second left reference electrode arm 621 and a second right reference electrode arm 623. All of the design considerations and possibilities regarding the left and right reference electrode arms 20, 22 of the device 10 of FIGS. 1A-C apply equally to the second left and right reference electrode arms 621, 623 of device 610 of FIG. 6. Although device 610 includes four reference electrode arms, in one or more alternative embodiments, the device 610 can include any suitable number of reference electrode arms.

The second left and right reference electrode arms 621, 623 can be attached to the sensor array portion 618 in any suitable location. In the illustrative embodiment, the second left and right reference electrode arms 621, 623 are attached to the sensor array portion 618 along a bottom edge 632 of the sensor array portion 618. The second left and right reference electrode arms 621, 623 can be attached in any suitable location along the bottom edge 632. In one or more embodiments, the second left and right reference electrode arms 621, 623 can be attached to the bottom edge 632 within a posterior portion 659 of the device 610 such that the arms can be positioned on the posterior surface of the torso. In one or more alternative embodiments, the first and second reference electrode arms 621, 623 can be attached to a top edge 630 of the sensor array portion 618 as is further described herein. In one or more alternative embodiments, one of the second left and right reference electrode arms 621, 623 can be attached to the top edge 630 and the other attached to the bottom edge 632.

The device 610 can also include a second left reference electrode 650 positioned on or in the second left electrode arm 621, and a second right reference electrode 652 positioned on or in the second right reference electrode arm 623. The second left and right reference electrodes 650, 652 can be positioned in any suitable location. For example, in one or more embodiments, the second left reference electrode 650 can be positioned proximate a distal end 654 of the second left reference electrode arm 621, and the second right reference electrode 652 can be positioned proximate a distal end 656 of the second right reference electrode arm 623. The second left and right reference electrodes 650, 652 can include any suitable reference electrodes, e.g., reference electrodes 72, 74 of device 10 of FIGS. 1A-C. And the second left and right reference electrodes 650, 652 can be electrically connected to a contact in a contact array 678 in the contact array arm 624 as is described further herein in reference to device 10 of FIGS. 1A-C.

In one or more embodiments, the sensor array portion 618 of the substrate 612 includes a left edge 626, a right edge 628, the top edge 630 extending from the left edge to the right edge, and the bottom edge 632 extending from the left edge to the right edge. In the illustrative embodiment, the device 610 can be configured such that an anterior portion 658 of the device can be positioned on an anterior surface of a torso of a patient, and a posterior portion 659 of the device can be positioned on a posterior surface of the torso.

In one or more embodiments, the left edge 626 and the right edge 628 of the sensor array portion 618 can be positioned on the posterior surface of the torso such that the left and right edges are adjacent to one another. Further, in one or more alternative embodiments, the left and right edges 626, 628 can overlap. In one or more embodiments, fasteners may be positioned on the sensor array portion 618 near one or both of the left and right edges 626, 628 such that these edges can be fastened together and the device 610 secured to a patient. Any suitable fasteners can be utilized.

Alternatively, in one or more embodiments, the sensor array portion 618 can be separated along a separation line to properly size the device 610 for a particular patient. For example, the device 610 can include a plurality of lines of weakness 660 in the sensor array portion 618 of the substrate 612, where each line of weakness of the plurality of lines of weakness is configured to enhance separation of the sensor array portion of the substrate along a separation line that extends between at least two sensors of the plurality of sensors 642. The substrate 612 can be separated along a first line of weakness 662 of the plurality of lines of weakness 660, where the first line of weakness extends between the top edge 630 and the bottom edge 632 of the sensor array portion 618, to remove part of the sensor array portion such that the device can be sized for a particular patient. The plurality of lines of weakness 660 can include any suitable lines of weakness, e.g., lines of weakness 62 of device 10 of FIGS. 1A-C. The sensor array portion 618 can further be separated along additional lines of weakness to properly size the device 610.

In one or more embodiments, the left and right edges 626, 628 can be positioned proximate a spine of a patient. As used herein, the term "proximate a spine of a patient" means that an element or feature is located closer to the spine than to a lateral surface of a torso of a patient. In one or more alternative embodiments, the left and right edges 626, 628 can be positioned proximate a lateral surface of a torso of a patient, e.g., the left side or the right lateral surface of the torso of the patient. As used herein, the term "proximate a lateral surface of a torso of a patient" means that an element or feature is located closer to the lateral surface of the torso than to the spine or sternum of a patient.

The device 610 of FIG. 6 can be applied using any suitable technique or combination of techniques. For example, the anterior portion 658 of the device 610 can first be applied to an anterior surface of a torso of a patient such that a center 613 of the device is proximate a sternum of the patient. As used herein, the term "proximate a sternum of a patient" means that an element or feature is located closer to the sternum than to a lateral surface of a torso or a spine of a patient.

The device 610 can include at least one alignment marker 670 that can aid in aligning the anterior portion 658 of the device 610 with the sternum. The at least one alignment marker 670 can include any suitable alignment marker or markers, e.g., at least one alignment marker 70 of device 10. The device 610 can be extended or wrapped around the torso, and, if necessary, one or more portions of the sensor array portion 618 of the device can be separated along a separation line or lines such that the device is appropriately sized for a particular patient, e.g., the sensors 642 are positioned in the desired locations on the torso. The posterior portion 659 of the device 610 can be applied to the posterior surface of the torso.

Figure 7:
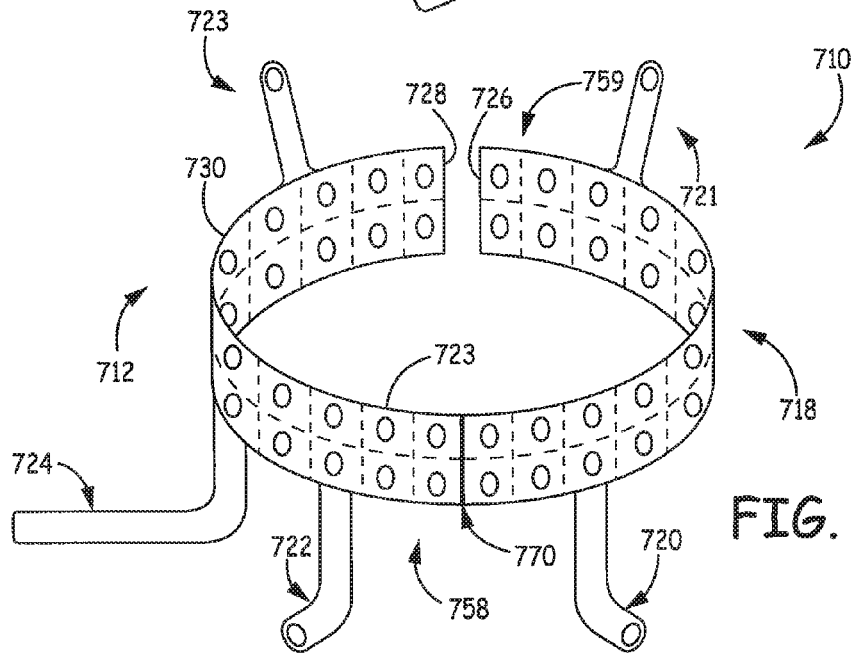
FIG. 7 is a schematic perspective view of another embodiment of a bioelectric sensor device.

FIG. 7 is a schematic perspective view of another embodiment of a bioelectric sensor device 710. The device 710 is similar to device 610 of FIG. 6. All of the design considerations and possibilities regarding the device 610 of FIG. 6 apply equally to the device 710 of FIG. 7. One difference between device 710 and device 610 is that second left and right reference electrode arms 721, 723 are attached to sensor array portion 718 at a top edge 730 of the sensor array portion. The second left and right reference electrode arms 721, 723 can be attached at any suitable location along the top edge 730. In one or more embodiments, the second left and right reference electrode arms 721, 723 can be attached to the top edge 730 within a posterior portion 759 of the device 710 such that the arms 721, 723 can be positioned on the posterior surface of the torso of the patient.

Another difference between devices 710 and 610 is that left and right reference electrode arms 720, 722 are attached to the sensor array portion 718 at a bottom edge 732 of the sensor array portion as previously described herein. The left and right reference electrode arms 720, 722 can be attached at any suitable location along the bottom edge 730. In one or more embodiments, the left and right reference electrode arms 720, 722 are attached to the bottom edge 732 within an anterior portion 758 of the device 710 such that the arms 720, 722 can be positioned on the anterior surface of the torso.

As mentioned herein, a contact array arm can be attached to a sensor array portion of the disclosed devices at any suitable location. For example, as illustrated in FIG. 7, contact array arm 724 is attached to the bottom edge 732 of the sensor array portion 718. The contact array arm 724 can be positioned in any suitable location along the bottom edge 732.

Figure 8:
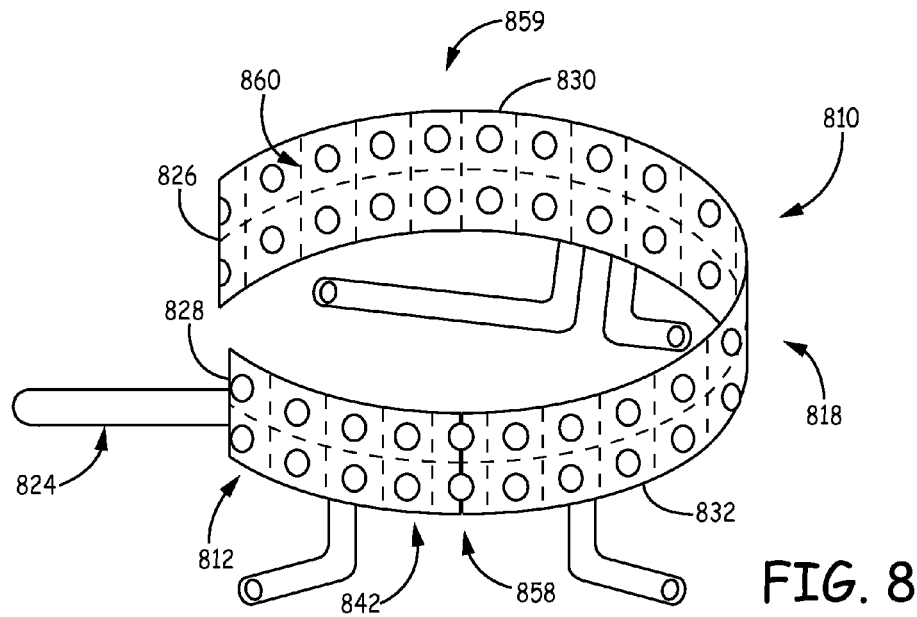
FIG. 8 is a schematic perspective view of another embodiment of a bioelectric sensor device.

In general, the disclosed devices can be configured such that the left and right edges of the sensor array portion of the device are positioned in any suitable location on a torso of a patient. For example, FIG. 8 is a schematic perspective view of another embodiment of a bioelectric sensor device 810. All of the design considerations and possibilities regarding the device 610 of FIG. 6 apply equally to the device 810 of FIG. 8. One difference between the device 810 and the device 610 is that a left edge 826 of a sensor array portion 818 of a substrate 812 of the device is configured to be positioned proximate a lateral surface of a torso of a patient. Further, a right edge 828 of the sensor array portion 818 is also configured to be positioned proximate the lateral surface.

Another difference between the device 810 of FIG. 8 and device 610 of FIG. 6 is that a contact array arm 824 is attached to the sensor array portion 818 at the right edge 828. The contact array arm 824 can be positioned in any suitable location along the right edge 828. In one or more alternative embodiments, the contact array arm 824 can be attached to the left edge 826 of the sensor array portion 818.

The device 810 can be positioned on a patient using any suitable technique or combination of techniques. For example, an anterior portion 858 of the device 810 can be positioned on the anterior surface of the torso. The device 810 can be extended or wrapped around the torso such that a posterior portion 859 of the device is positioned on the posterior surface of the torso. In one or more embodiments, one or more portions of the sensor array portion 818 of the device 810 can be separated from the substrate 812 along one or more lines of weakness of the plurality of lines of weakness 860 such that plurality of sensors 842 are positioned in desired locations on the torso.

Figure 9:
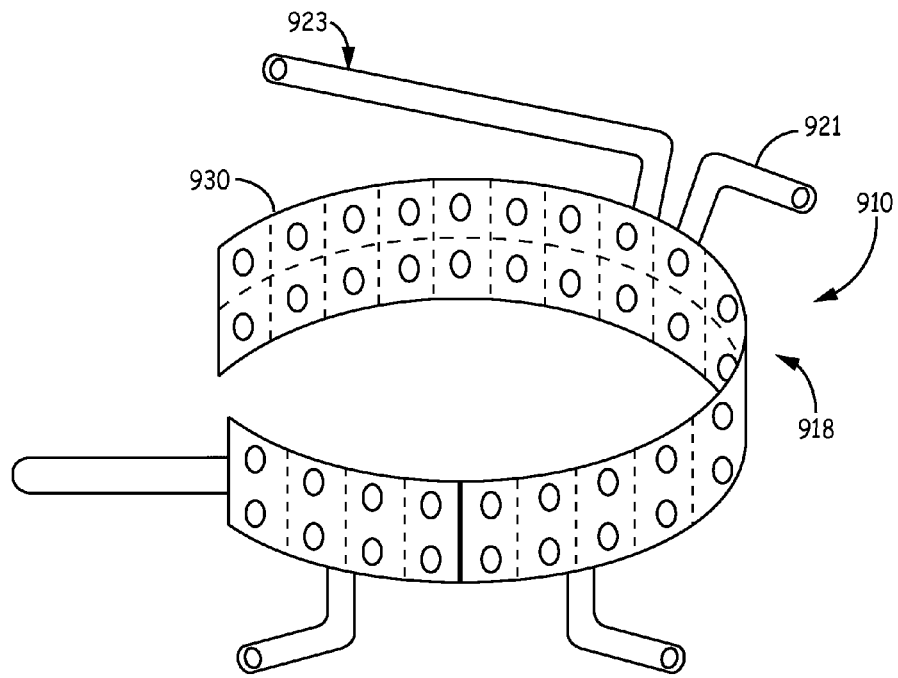
FIG. 9 is a schematic perspective view of another embodiment of a bioelectric sensor device.

As described herein, the reference electrode arms can be attached to the sensor array portion of the substrate in any suitable location. For example, FIG. 9 is a schematic perspective view of another embodiment of a bioelectric sensor device 910. All of the design considerations and possibilities regarding the device 810 of FIG. 8 apply equally to the device 910 of FIG. 9. One difference between device 810 and device 910 is that second left and right reference electrode arms 921, 923 are attached to sensor array portion 918 at a top edge 930.

Figure 10:
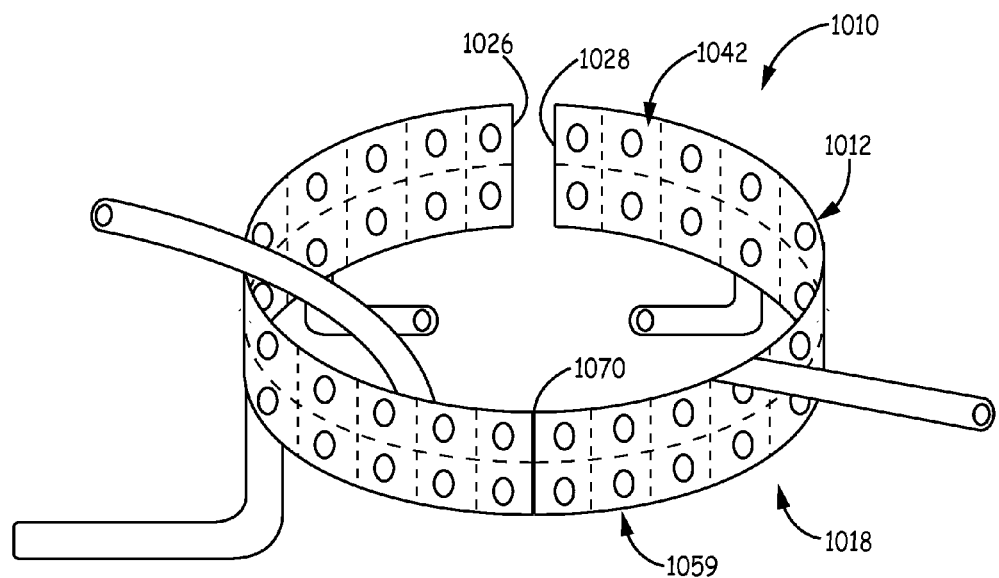
FIG. 10 is a schematic perspective view of another embodiment of a bioelectric sensor device.

The bioelectric sensor devices of the present disclosure can be applied using any suitable technique or combination of techniques. For example, the device 610 of FIG. 6 can first be applied to the anterior, posterior, or lateral surfaces of a torso of a patient. In one or more embodiments, the devices disclosed herein can be designed to be placed on a posterior surface of the torso prior to being placed on the anterior surface. For example, FIG. 10 is a schematic perspective view of another embodiment of a bioelectric sensor device 1010 that is configured to first be placed on the posterior surface of the torso. All of the design considerations and possibilities regarding the device 610 of FIG. 6 apply equally to the device 1010 of FIG. 10.

One difference between the device 610 and the device 1010 is that the device 1010 is configured to first be applied to the posterior surface of the torso. For example, the device 1010 can include at least one alignment marker 1070 on a posterior portion 1059 of the device that is configured to be positioned proximate the spine of the patient. As used herein, the phrase "proximate the spine of the patient" means that an element of aspect of a device is positioned closer to the spine than to lateral surfaces or the sternum of the torso.

After the device 1010 is positioned on the posterior surface of the torso, left and right edges 1026, 1028 can be extended or wrapped around the torso such that they are on the anterior surface of the torso. One or more portions of the sensor array portion 1018 of substrate 1012 can be separated from the substrate along one or more separation lines near one or both of the left and right edges 1026, 1028 of the device such that the device is appropriately sized to fit a particular patient, e.g., a plurality of sensors 1042 are positioned in their desired locations on the torso of the patient.

Figure 11:
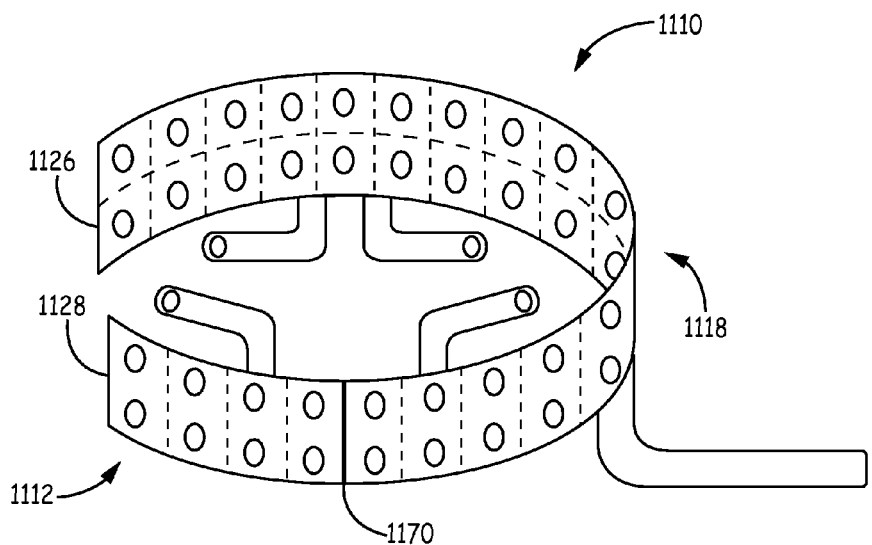
FIG. 11 is a schematic perspective view of another embodiment of a bioelectric sensor device.

Alternatively, the dimensions of the devices disclosed herein can be selected such that the left and right edges of the sensor array portion are positioned proximate a lateral surface of a torso of a patient. For example, FIG. 11 is a schematic perspective view of another embodiment of a bioelectric sensor device 1110. All of the design considerations and possibilities regarding the device 610 of FIG. 6 apply equally to the device 1110 of FIG. 11.

One difference between device 1110 and device 610 is that device 1110 is configured to first be applied to a posterior surface of a torso of a patient. For example, the device 1110 can include at least one alignment marker 1170 that is configured to be aligned with a spine of a patient. Another difference is that the device 1110 is configured such that left and right edges 1126, 1128 are positioned proximate a lateral surface of the torso when the device is positioned on a patient.

The device 1110 can be sized to fit a particular patient by removing one or more portions of sensor array portion 1118 of substrate 1112 by separating the sensor array portion along one or more separation lines as is further described herein. These one or more portions can be removed proximate one or both of the left and right edges 1126, 1128 of sensor array portion 1118.

The bioelectric sensor devices described herein can be used with any suitable medical monitoring system or apparatus. Exemplary medical monitoring systems and methods that use these systems may be described in U.S. patent application Ser. No. 13/916,353, filed on Jun. 12, 2013, and entitled IMPLANTABLE ELECTRODE LOCATION SELECTION; U.S. patent application Ser. No. 13/916,377, filed on Jun. 12, 2013, and entitled IMPLANTABLE ELECTRODE LOCATION SELECTION; U.S. Provisional Patent Application No. 61/817,483, filed on Apr. 30, 2013, and entitled IDENTIFYING EFFECTIVE ELECTRODES; U.S. Provisional Patent Application No. 61/817,480, filed on Apr. 30, 2013, and entitled IDENTIFYING OPTICAL ELECTRICAL VECTORS; U.S. Provisional Patent Application No. 61/913,795, filed on Dec. 9, 2013, and entitled SYSTEMS, METHODS, AND INTERFACES FOR IDENTIFYING EFFECTIVE ELECTRODES; U.S. Provisional Patent Application No. 61/913,784, filed on Dec. 9, 2013, and entitled SYSTEMS, METHODS, AND INTERFACES FOR IDENTIFYING OPTIMAL ELECTRICAL VECTORS; U.S. patent application entitled SYSTEMS, METHODS, AND INTERFACES FOR IDENTIFYING EFFECTIVE ELECTRODES and filed on even date herewith; U.S. patent application entitled SYSTEMS, METHODS, AND INTERFACES FOR IDENTIFYING OPTIMAL ELECTRICAL VECTORS and filed on even date herewith; and U.S. patent application entitled NONINVASIVE CARDIAC THERAPY EVALUATION and filed on even date herewith, each of which are incorporated herein by reference in their entireties.

Figure 5:
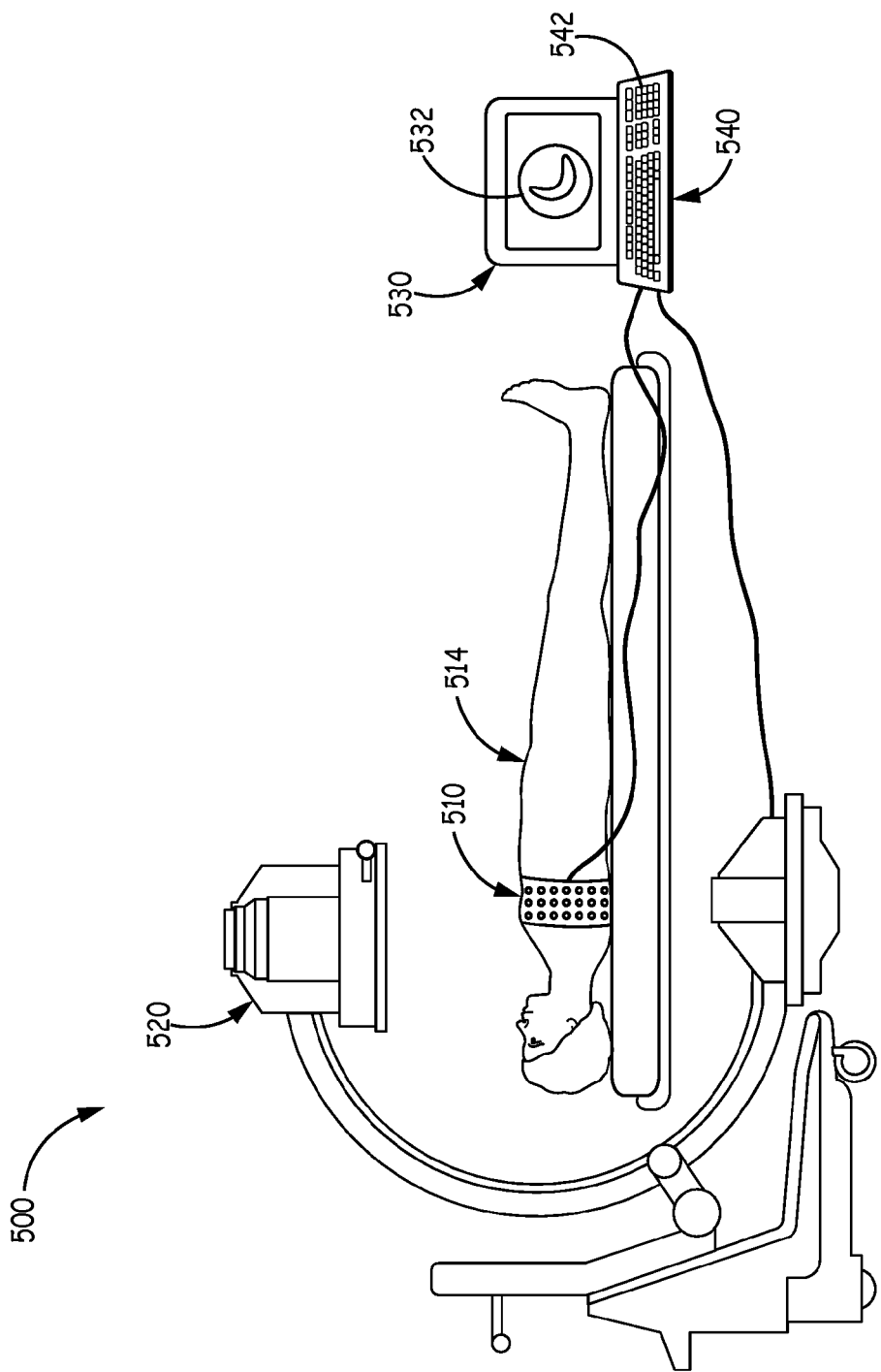
FIG. 5 is a schematic side view of a system that includes a bioelectric sensor device.

For example, various exemplary systems, methods, and interfaces may be configured to use electrode apparatus including bioelectric sensor devices, imaging apparatus, display apparatus, and computing apparatus to noninvasively assist a user (e.g., a physician) in selecting one or more locations (e.g., implantation site regions) proximate a patient's heart for one or more implantable electrodes and/or to navigate one or more implantable electrodes to the selected location(s). An exemplary system 500 including bioelectric sensor device 510, imaging apparatus 520, display apparatus 530, and computing apparatus 540 is depicted in FIG. 5.

The sensor device 510, which can include any suitable sensor device described herein (e.g., sensor device 10 of FIGS. 1A-C), is operatively coupled to the computing apparatus 540 (e.g., through contact array 78) to provide electrical signals from each of the sensors (e.g., sensors of the plurality of sensors 42) to the computing apparatus 540 for analysis.

The imaging apparatus 520 may be any type of imaging apparatus configured to image, or provide images of, at least a portion of the patient in a non-invasive manner. For example, the imaging apparatus 520 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in selecting a location proximate a patient's heart for an implantable electrode, and after the exemplary systems, methods, and interfaces have provided noninvasive assistance, the exemplary systems, methods, and interfaces may then provide assistance to implant, or navigate, an implantable electrode into the patient, e.g., proximate the patient's heart.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 520 may be configured to capture, or take, x-ray images (e.g., two dimensional x-ray images, three dimensional x-ray images, etc.) of the patient 514. The imaging apparatus 520 may be operatively coupled (e.g., through one or wired electrical connections, wirelessly, etc.) to the computing apparatus 540 such that the images captured by the imaging apparatus 520 may be transmitted to the computing apparatus 540. Further, the computing apparatus 540 may be configured to control the imaging apparatus 520 to, e.g., configure the imaging apparatus 520 to capture images, change one or more settings of the imaging apparatus 520, etc.

It will be recognized that while the imaging apparatus 520 as shown in FIG. 5 may be configured to capture x-ray images, any other alternative imaging modality may also be used by the exemplary systems, methods, and interfaces described herein. For example, the imaging apparatus 520 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 520 may be configured to capture a plurality of consecutive images (e.g., continuously) to provide video frame data. In other words, a plurality of images taken over time using the imaging apparatus 520 may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 530 and the computing apparatus 540 may be configured to display and analyze data such as, e.g., surrogate electrical activation data, image data, mechanical motion data, etc. gathered, or collected, using the sensor device 510 and the imaging apparatus 520 to noninvasively assist a user in location selection of an implantable electrode. In at least one embodiment, the computing apparatus 540 may be a server, a personal computer, or a tablet computer. The computing apparatus 540 may be configured to receive input from input apparatus 542 and transmit output to the display apparatus 530. Further, the computing apparatus 540 may include data storage that may allow for access to processing programs or routines and/or and one or more other types of data, e.g., for driving a graphical user interface configured to noninvasively assist a user in location selection of an implantable electrode, etc.

The computing apparatus 540 may be operatively coupled to the input apparatus 542 and the display apparatus 530 to, e.g., transmit data to and from each of the input apparatus 542 and the display apparatus 530. For example, the computing apparatus 540 may be electrically coupled to each of the input apparatus 542 and the display apparatus 530 using, e.g., analog electrical connections, digital electrical connections, wireless connections, bus-based connections, network-based connections, internet-based connections, etc. As described further herein, a user may provide input to the input apparatus 542 to manipulate, or modify, one or more graphical depictions displayed on the display apparatus 530 to view and/or selected one or more target or candidate locations of a portion of a patient's heart as further described herein.

Although as depicted the input apparatus 542 is a keyboard, it is to be understood that the input apparatus may include any apparatus capable of providing input to the computing apparatus 540 to perform the functionality, methods, and/or logic described herein. For example, the input apparatus 542 may include a mouse, a trackball, a touchscreen (e.g., capacitive touchscreen, a resistive touchscreen, a multi-touch touchscreen, etc.), etc. Likewise, the display apparatus 530 may include any apparatus capable of displaying information to a user, such as a graphical user interface 532 including graphical depictions of anatomy of a patient's heart, images of a patient's heart, graphical depictions of locations of one or more electrodes, graphical depictions of one or more target or candidate locations, alphanumeric representations of one or more values, graphical depictions or actual images of implanted electrodes and/or leads, etc. For example, the display apparatus 530 may include a liquid crystal display, an organic light-emitting diode screen, a touchscreen, a cathode ray tube display, etc.

The graphical user interfaces 532 displayed by the display apparatus 530 may include, or display, one or more regions used to display graphical depictions, to display images, to allow selection of one or more regions or areas of such graphical depictions and images, etc. As used herein, a "region" of a graphical user interface 532 may be defined as a portion of the graphical user interface 532 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 532 may be defined as a portion of the graphical user interface 532 located with a region that is smaller than the region it is located within.

The processing programs or routines stored and/or executed by the computing apparatus 540 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, or any other processing required to implement one or more exemplary methods and/or processes described herein. Data stored and/or used by the computing apparatus 540 may include, for example, image data from the imaging apparatus 520, electrical signal data from the sensor device 510, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 540 may be, for example, any fixed or mobile computer system (e.g., a controller, a microcontroller, a personal computer, mini computer, tablet computer, etc.). The exact configuration of the computing apparatus 530 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 540 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A bioelectric sensor device for sensing bioelectric data from a human body, the device comprising:
a flexible dielectric substrate comprising a first major surface and a second major surface, wherein the substrate further comprises a sensor array portion comprising a center, a left reference electrode arm comprising a proximal end and a distal end, a right reference electrode arm comprising a proximal end and a distal end, and a contact array arm comprising a proximal end and a distal end, wherein the proximal end of the contact array arm is attached to the sensor array portion of the substrate;
a plurality of sensors arranged in a sensor array on the sensor array portion of the substrate, wherein each sensor of the plurality of sensors is configured to sense bioelectric data when in contact with skin;
an electrically conductive network located on the substrate, wherein the electrically conductive network comprises a plurality of electrically conductive paths, wherein each electrically conductive path of the plurality of electrically conductive paths extends from one sensor of the plurality of sensors to a contact array on the contact array arm, wherein the contact array comprises a plurality of contacts on the contact array arm proximate the distal end of the contact array arm;
a left reference electrode proximate the distal end of the left reference electrode arm and a right reference electrode proximate the distal end of the right reference electrode arm, wherein the left reference electrode is electrically connected to a contact in the contact array and the right reference electrode is electrically connected to a contact in the contact array; and
a plurality of lines of weakness formed in the sensor array portion of the substrate, wherein each line of weakness of the plurality of lines of weakness is configured to enhance separation of the sensor array portion of the substrate along a separation line that extends between at least two sensors of the plurality of sensors.

2. A device according to claim 1, wherein the sensor array portion of the substrate comprises a left edge, a right edge, a top edge extending from the left edge to the right edge, and a bottom edge extending from the left edge to the right edge, and wherein a first line of weakness of the plurality of lines of weakness extends between the top edge and the bottom edge of the sensor array portion, and further wherein a first sensor of the plurality of sensors is located between the first line of weakness and the left edge of the sensor array portion such that separation of the substrate along the first line of weakness removes the first sensor from the device.

3. A device according to claim 2, wherein a second line of weakness of the plurality of lines of weakness extends between the top edge and the bottom edge of the sensor array portion, and further wherein a second sensor of the plurality of sensors is located between the second line of weakness and the first line of weakness such that separation of the substrate along the second line of weakness removes the second sensor from the device.

4. A device according to claim 3, wherein a third line of weakness of the plurality of lines of weakness extends between the top edge and the bottom edge of the sensor array portion, and further wherein a third sensor of the plurality of sensors is located between the third line of weakness and the second line of weakness such that separation of the substrate along the third line of weakness removes the third sensor from the device.

5. A device according to claim 4, wherein a fourth line of weakness of the plurality of lines of weakness extends between the first line of weakness and the second line of weakness such that separation of the substrate along the first, second, and fourth lines of weakness removes the second sensor of the plurality of sensors from the device without removing the first sensor and wherein an electrically conductive path of the plurality of electrically conductive paths that extends from the first sensor to the contact array remains after separation of the second sensor.

6. A device according to claim 5, wherein a fifth line of weakness of the plurality of lines of weakness extends between the left edge and the center of the sensor array portion, wherein any of the lines of weakness of the plurality of lines of weakness that extend between the top edge and the bottom edge of the sensor array portion between the left edge and the center of the sensor array portion intersect the fifth line of weakness.

7. A device according to claim 6, wherein at least one sensor of the plurality of sensors is located between the fifth line of weakness and the top edge of the sensor array portion and wherein at least one sensor of the plurality of sensors is located between the fifth line of weakness and the bottom edge of the sensor array portion.

8. A device according to claim 7, wherein a sixth line of weakness of the plurality of lines of weakness extends between the right edge and the center of the sensor array portion, wherein any of the lines of weakness of the plurality of lines of weakness that extend between the top edge and the bottom edge of the sensor array portion between the right edge and the center of the sensor array portion intersect with the sixth line of weakness.

9. A device according to claim 8, wherein at least one sensor of the plurality of sensors is located between the sixth line of weakness and the top edge of the sensor array portion and wherein at least one sensor of the plurality of sensors is located between the sixth line of weakness and the bottom edge of the sensor array portion.

10. A device according to claim 2, further comprising at least one alignment marker positioned on the substrate and extending between the top edge and the bottom edge of the sensor array portion at the center of the sensor array portion.

11. A device according to claim 10, wherein the at least one alignment marker comprises radiopaque material.

12. A device according to claim 1, wherein the sensor array portion of the substrate comprises a left edge, a right edge, a top edge extending from the left edge to the right edge, and a bottom edge extending from the left edge to the right edge, wherein the proximal end of the left reference electrode arm and the proximal end of the right reference electrode arm are attached to the sensor array portion of the flexible dielectric substrate.

13. A device according to claim 12, wherein the proximal end of the left reference electrode arm and the proximal end of the right reference electrode arm are attached to the bottom edge of the sensor array portion of the flexible dielectric substrate.

14. A device according to claim 12, wherein the proximal end of the left reference electrode arm and the proximal end of the right reference electrode arm are attached to the top edge of the sensor array portion of the flexible dielectric substrate.

15. A device according to claim 12, wherein the proximal end of the left reference electrode arm is located inside the plurality of lines of weakness such that the left reference electrode arm remains attached to the sensor array portion of the flexible dielectric substrate after separation of the sensor array portion along any line of weakness of the plurality of lines of weakness.

16. A device according to claim 12, wherein the proximal end of the right reference electrode arm is located inside the plurality of lines of weakness such that the right reference electrode arm remains attached to the sensor array portion of the flexible dielectric substrate after separation of the sensor array portion along any line of weakness of the plurality of lines of weakness.

17. A device according to claim 1, wherein the proximal end of the left reference electrode arm and the proximal end of the right reference electrode arm are attached to the contact array arm of the flexible dielectric substrate.

18. A device according to claim 1, wherein the sensor array portion of the substrate comprises a left edge, a right edge, a top edge extending from the left edge to the right edge, and a bottom edge extending from the left edge to the right edge, wherein the proximal end of the contact array arm is attached to the bottom edge of the sensor array portion.

19. A device according to claim 1, wherein the contact array arm comprises adhesive on the second major surface of the substrate proximate the proximal end of the contact array arm.

20. A device according to claim 1, wherein the flexible dielectric substrate further comprises a second left reference electrode arm comprising a proximal end and a distal end, and a second right reference electrode arm comprising a proximal end and a distal end.

21. A device according to claim 20, further comprising a second left reference electrode proximate the distal end of the second left reference electrode arm and a second right reference electrode proximate the distal end of the second right reference electrode arm, wherein the second left reference electrode is electrically connected to a contact in the contact array and the second right reference electrode is electrically connected to a contact in the contact array.

22. A device according to claim 21, wherein the sensor array portion of the substrate comprises a left edge, a right edge, a top edge extending from the left edge to the right edge, and a bottom edge extending from the left edge to the right edge, wherein the proximal end of the second left reference electrode arm and the proximal end of the second right reference electrode arm are attached to the sensor array portion of the flexible dielectric substrate.

23. A device according to claim 22, wherein the proximal end of the second left reference electrode arm and the proximal end of the second right reference electrode arm are attached to the bottom edge of the sensor array portion of the flexible dielectric substrate.

24. A device according to claim 22, wherein the proximal end of the second left reference electrode arm and the proximal end of the second right reference electrode arm are attached to the top edge of the sensor array portion of the flexible dielectric substrate.

25. A device according to claim 22, wherein the proximal end of the second left reference electrode arm is located inside the plurality of lines of weakness such that the second left reference electrode arm remains attached to the sensor array portion of the flexible dielectric substrate after separation of the sensor array portion along any line of weakness of the plurality of lines of weakness.

26. A device according to claim 22, wherein the proximal end of the second right reference electrode arm is located inside the plurality of lines of weakness such that the second right reference electrode arm remains attached to the sensor array portion of the flexible dielectric substrate after separation of the sensor array portion along any line of weakness of the plurality of lines of weakness.

27. A method of removing a sensor of the plurality of sensors from a bioelectric sensor device, comprising:
  providing a bioelectric sensor device according to claim 1, wherein the sensor array portion of the substrate comprises a left edge, a right edge, a top edge extending from the left edge to the right edge, and a bottom edge extending from the left edge to the right edge; and
  separating the sensor array portion of the substrate along a line of weakness of the plurality of lines of weakness that extends between the top edge and the bottom edge of the sensor array portion, wherein the sensor is located between the line of weakness and the left edge of the sensor array portion.

28. A method according to claim 27, further comprising removing an additional sensor of the plurality of sensors by separating the sensor array portion of the substrate along an additional line of weakness that extends between the top edge and the bottom edge of the sensor array portion, wherein the additional sensor is located between the additional line of weakness and the right edge of the sensor array portion.

* * * * *